United States Patent
Ji

(10) Patent No.: US 12,189,015 B2
(45) Date of Patent: Jan. 7, 2025

(54) COIL ASSEMBLY OF MAGNETIC RESONANCE IMAGING DEVICE

(71) Applicant: SHANGHAI UNITED IMAGING HEALTHCARE CO., LTD., Shanghai (CN)

(72) Inventor: Ling Ji, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 93 days.

(21) Appl. No.: 18/059,405

(22) Filed: Nov. 28, 2022

(65) Prior Publication Data
US 2023/0106862 A1   Apr. 6, 2023

Related U.S. Application Data

(63) Continuation of application No. 17/243,541, filed on Apr. 28, 2021, now Pat. No. 11,513,179, which is a
(Continued)

(30) Foreign Application Priority Data

Jul. 13, 2018   (CN) .......................... 201821115673.1
Jan. 29, 2019   (CN) .......................... 201920155186.6

(51) Int. Cl.
*G01V 3/00*       (2006.01)
*A61B 5/055*     (2006.01)
(Continued)

(52) U.S. Cl.
CPC .......... *G01R 33/5673* (2013.01); *A61B 5/055* (2013.01); *A61B 5/1102* (2013.01);
(Continued)

(58) Field of Classification Search
CPC ....................................................... A61G 1/02
(Continued)

(56) References Cited

U.S. PATENT DOCUMENTS 5,989,397 A * 11/1999 Laube ..................... C23C 14/22
                                                               118/620
6,535,754 B2    3/2003 Fishbein et al.
(Continued)

FOREIGN PATENT DOCUMENTS

CN       101855564 A  * 10/2010  .......... A61B 5/0035
CN       104545859 A  *  4/2015  .......... A61B 5/0004
(Continued)

*Primary Examiner* — Walter L Lindsay, Jr.
*Assistant Examiner* — Frederick Wenderoth
(74) *Attorney, Agent, or Firm* — METIS IP LLC

(57) ABSTRACT

The present disclosure relates to a coil assembly of an MRI device. The MRI device may be configured to perform an MR scan on a subject. The coil assembly may include one or more coil units, a substrate, and a sensor mounted within or on the substrate. The one or more coil units may be configured to receive an MR signal from the subject during the MR scan. The substrate may be configured to position the one or more coil units during the MR scan. The one or more coil units may be mounted within or on the substrate. The sensor may be configured to detect a motion signal relating to a physiological motion of the subject before or during the MR scan.

20 Claims, 14 Drawing Sheets

Related U.S. Application Data continuation of application No. 16/510,342, filed on Jul. 12, 2019, now Pat. No. 11,002,816.

(51) Int. Cl.
  *A61B 5/11* (2006.01)
  *A61B 5/113* (2006.01)
  *A61B 5/25* (2021.01)
  *G01R 33/38* (2006.01)
  *G01R 33/567* (2006.01)

(52) U.S. Cl.
  CPC ............... *A61B 5/113* (2013.01); *A61B 5/25* (2021.01); *G01R 33/38* (2013.01); *A61B 2562/0219* (2013.01); *A61B 2562/0247* (2013.01)

(58) Field of Classification Search
  USPC ........................................................ 324/318
  See application file for complete search history.

(56) References Cited

U.S. PATENT DOCUMENTS

| | | | |
|---|---|---|---|
| 11,002,816 | B2 | 5/2021 | Ji |
| 2004/0100262 | A1 | 5/2004 | Seeber |
| 2005/0107685 | A1 | 5/2005 | Seeber |
| 2009/0062640 | A1 | 3/2009 | Miyoshi |
| 2012/0310060 | A1* | 12/2012 | Baker, Jr. ............ A61B 5/14551 600/324 |
| 2013/0116743 | A1* | 5/2013 | Karamanoglu ...... A61N 1/3629 607/42 |
| 2015/0335268 | A1 | 11/2015 | Biber et al. |
| 2016/0165338 | A1* | 6/2016 | Benattar ................ H04R 1/406 381/92 |
| 2017/0258409 | A1 | 9/2017 | Do et al. |
| 2020/0018808 | A1* | 1/2020 | Ji ........................ G01R 33/5673 |
| 2021/0116519 | A1 | 4/2021 | Weiss |

FOREIGN PATENT DOCUMENTS

| | | | | |
|---|---|---|---|---|
| CN | 205488132 U | * | 8/2016 | |
| DE | 102014208650 A1 | * | 11/2015 | ............ A61B 5/0456 |
| JP | 2016216448 A | * | 12/2016 | ............ C07D 471/04 |
| JP | 2018027152 A | | 2/2018 | |
| WO | 2001067952 A1 | | 9/2001 | |
| WO | WO-2010024290 A1 | * | 3/2010 | ............ A61B 5/0059 |
| WO | WO-2015007695 A1 | * | 1/2015 | ........ G01R 33/34007 |

\* cited by examiner

800A

800B

1000

COIL ASSEMBLY OF MAGNETIC RESONANCE IMAGING DEVICE

CROSS-REFERENCE TO RELATED APPLICATIONS

This application is a continuation of U.S. patent application Ser. No. 17/243,541, filed on Apr. 28, 2021, which is a continuation of U.S. patent application Ser. No. 16/510,342 (now U.S. Pat. No. 11,002,816), filed on Jul. 12, 2019, which claims priority to Chinese Patent Application No. 201920155186.6, filed on Jan. 29, 2019 and Chinese Patent Application No. 201821115673.1, filed on Jul. 13, 2018, the contents of each of which are hereby incorporated by reference.

TECHNICAL FIELD

The present disclosure generally relates to magnetic resonance imaging (MRI) device, and in particular, to a coil assembly of an MRI device.

BACKGROUND

Magnetic resonance imaging (MRI) devices are widely used in medical imaging. A subject, such as a patient, may be scanned by an MRI device, and a coil assembly of the MRI device may be used to detect MR signals generated during the scan. In some occasions, the subject may undergo a physiological motion (e.g., a cardiac motion, a respiratory motion, etc.) during an MR scan, which may affect imaging quality, for example, result in motion artifacts in a resulting MR image. A motion signal relating to the physiological motion may need to be detected and taken into consideration in MRI. Conventionally, a motion signal detection device independent from the coil assembly may be used to detect a motion signal, and the equipment complexity and cost may increase. For example, during a scan on the chest of a patient, one or more electrodes (e.g., four electrodes representing four limbs of the patient) may be placed on the skin of the patient to detect an electrocardiogram (ECG) signal representing the cardiac motion of the patient. The electrode(s) may be fixed on the patient by a user (e.g., a doctor) and connected to wires, which may cause a potential safety risk. As another example, a belt tied around the chest of the patient and/or a pressure measurement sensor may be utilized to measure a respiratory signal of the patient. Alternatively, the patient may be trained to breathe at a certain pace and amplitude during the MR scan, which is difficult and time-consuming. Thus, it is desirable to provide a coil assembly which is capable of detecting both MR signals and motion signals, and effective systems and methods for detecting a motion signal in MRI using the coil assembly, thereby reducing or mitigate the effect of the physiological motion and improve imaging quality.

SUMMARY

According to an aspect of the present disclosure, a coil assembly of an MRI device is provided. The MRI device may be configured to perform an MR scan on a subject. The coil assembly may include one or more coil units, a substrate, and a sensor mounted within or on the substrate. The one or more coil units may be configured to receive an MR signal from the subject during the MR scan. The substrate may be configured to position the one or more coil units during the MR scan. The one or more coil units may be mounted within or on the substrate. The sensor may be configured to detect a motion signal relating to a physiological motion of the subject before or during the MR scan.

In some embodiments, the substrate may include a proximal surface and a distal surface with respect to the subject. The proximal surface and the distal surface may be opposite to each other. The sensor may be mounted on the proximal surface of the substrate.

In some embodiments, the physiological motion may include a cardiac motion of the subject, and the sensor may include an electrocardiogram (ECG) sensor configured to detect a signal relating to the cardiac motion of the subject. The ECG sensor may further include a signal emitter and a signal receiver. The signal emitter may be configured to emit a reference signal toward the subject, and the reference signal may be reflected by the subject. The signal receiver may be configured to receive at least a portion of the reflected reference signal from the subject.

In some embodiments, the signal emitter may include a signal generator configured to generate a preliminary reference signal, a signal amplifier configured to generate the reference signal by amplifying the preliminary reference signal, and a transmitting antenna configured to emit the reference signal toward the subject.

In some embodiments, the signal receiver may include a receiving antenna, a signal amplifier, and a signal mixer. The receiving antenna may be configured to receive the at least a portion of the reflected reference signal. The signal amplifier may be configured to amplify the received portion of the reflected reference signal. The signal mixer may be configured to generate a mixed signal by mixing the reference signal with the amplified portion of the reflected reference signal. The mixed signal may be the signal relating to the cardiac motion of the subject.

In some embodiments, the signal receiver may further include a receiving antenna configured to receive at least a portion of the reflected reference signal, a signal amplifier configured to amplify the received portion of the reflected reference signal, and a signal mixer configured to generate a mixed signal by mixing the reference signal with the amplified portion of the reflected reference signal. The MRI device may further include a signal processing component configured to determine the signal relating to the cardiac motion of the subject based on the mixed signal.

In some embodiments, the signal processing component may be integrated into the ECG sensor.

In some embodiments, at least a portion of the signal receiver may be integrated into the one or more coil units.

In some embodiments, the reference signal may be a continuous wave signal with a time-varying frequency.

In some embodiments, the substrate may include at least one of fabric, plastic, polyethylene (PE), polypropylene (PP), polyester, ethylene-vinyl acetate (EVA), polybutylene terephthalate (PBT), polycarbonate (PC), polyoxymethylene (POM), polyurethane (PU), polystyrene (PS), nylon, cotton, fiber, or resin.

In some embodiments, the physiological motion may include a respiratory motion of the subject, and the sensor may include a respiratory signal detector configured to detect a signal relating to the respiratory motion of the subject.

In some embodiments, the respiratory signal detector may include a motion sensor and a pad. The motion sensor may be configured to detect a signal relating to the respiratory motion of the subject. The motion sensor may include at least one of a pressure sensor, an accelerometer, a speed sensor, or a gravity sensor. The pad may be configured to accommodate the motion sensor. The pad may be configured to accommodate the motion sensor.

In some embodiments, the coil assembly may further include a signal transmission component. The signal transmission component may be operably connected to the sensor and configured to transmit the motion signal to a control device of the MRI device. The control device may be configured to control the MRI device according to the motion signal.

In some embodiments, the coil assembly may further include an MR signal processing device. The MR signal processing device may be operably connected to the one or more coil units and the signal transmission component. The MR signal processing device may be configured to process the MR signal and transmit the processed MR signal to the signal transmission component. The signal transmission component may be further configured to transmit the processed MR signal to the control device.

In some embodiments, the MR signal processing device may include an LNA and a filter. The LNA may be configured to amplify the MR signal. The filter may be configured to generate the processed MR signal by filtering the amplified MR signal.

In some embodiments, the substrate may include two or more layers that form a chamber, and at least a portion of the one or more coil units and the sensor may be mounted within the chamber.

According to another aspect of the present disclosure, an MRI system is provided. The system may include an MRI device, at least one storage device, and at least one processor. The MRI device may include a coil assembly. The coil assembly may include one or more coil units, a substrate configured to position the coil assembly during an MR scan of a subject, and a sensor mounted within or on the substrate. The sensor may be configured to detect a motion signal of the subject. The at least one storage device may include a set of instructions, and the at least one processor may be configured to communicate with the at least one storage device and the MRI device. When executing the set of instructions, the at least one processor may be configured to direct the system to perform the following operations. The system may receive a motion signal relating to a physiological motion of the subject from the sensor before or during the MR scan of the subject. The system may determine a control signal based on the motion signal by the at least one processor. The system may transmit the control signal to the MRI device. The system may also apply the MR scan to the subject by the MRI device according to the control signal. The system may further receive one or more MR signals of the subject from the one or more coil units.

In some embodiments, to transmit a control signal to control the MRI device according to the motion signal, the system may determine an MR signal acquisition time based on the motion signal. The system may also transmit the control signal to the MRI device at the MR signal acquisition time. The control signal may further cause the MRI device to execute the MR scan at the MR signal acquisition time.

In some embodiments, the motion signal may be received from the sensor during the MR scan, and to transmit a control signal to control the MRI device according to the motion signal, the system may perform additional operations. The system may determine whether the physiological motion of the subject is smooth based on the motion signal. The system may transmit the control signal to the MRI device. The control signal may cause the MRI device to terminate or pause the MR scan.

In some embodiments, the system may reconstruct one or more MR images of the subject based on the one or more MR signals of the subject. The system may also correct the one or more MR images based on the motion signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
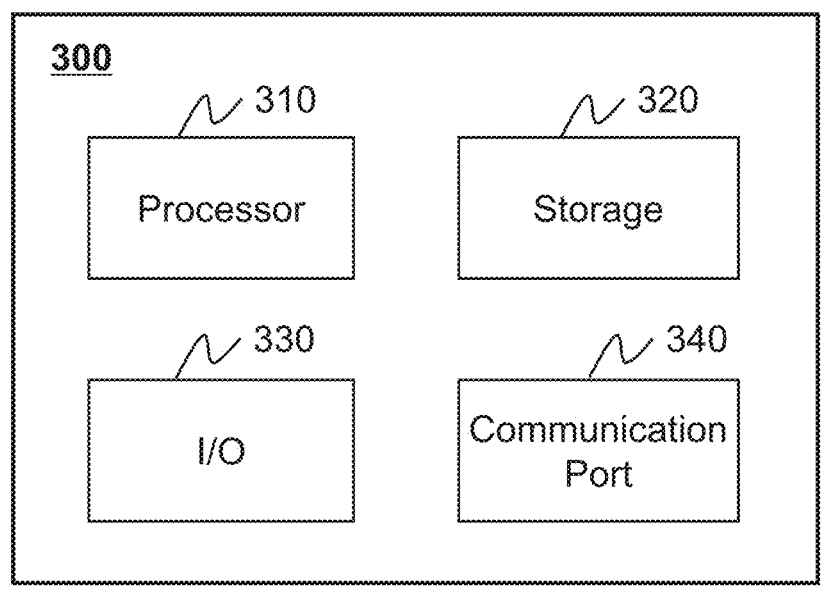
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a coil assembly of an MRI device. The MRI device may be configured to perform an MR scan on a subject. The coil assembly may include one or more coil units, a substrate, and a sensor. The coil unit(s) may be mounted within or on the substrate and configured to receive an MR signal from the subject during the MR scan. The substrate may be configured to position the one or more coil units and/or the sensor during the MR scan. The sensor may be mounted within or on the substrate configured to detect a motion signal relating to a physiological motion of the subject before or during the MR scan. For example, the sensor may include an ECG sensor configured to detect an ECG signal relating to a cardiac motion of the subject and/or a respiratory signal detector configured to detect a respiratory signal relating to a respiratory motion of the subject.

According to some embodiments of the present disclosure, the sensor for detecting a motion signal may be part of a coil assembly. Compared with using a motion signal detection device independent from the coil assembly, using a coil assembly incorporating a motion signal detection device may improve the utilization of the coil assembly and reduce system complexity and cost.

Figure 1:
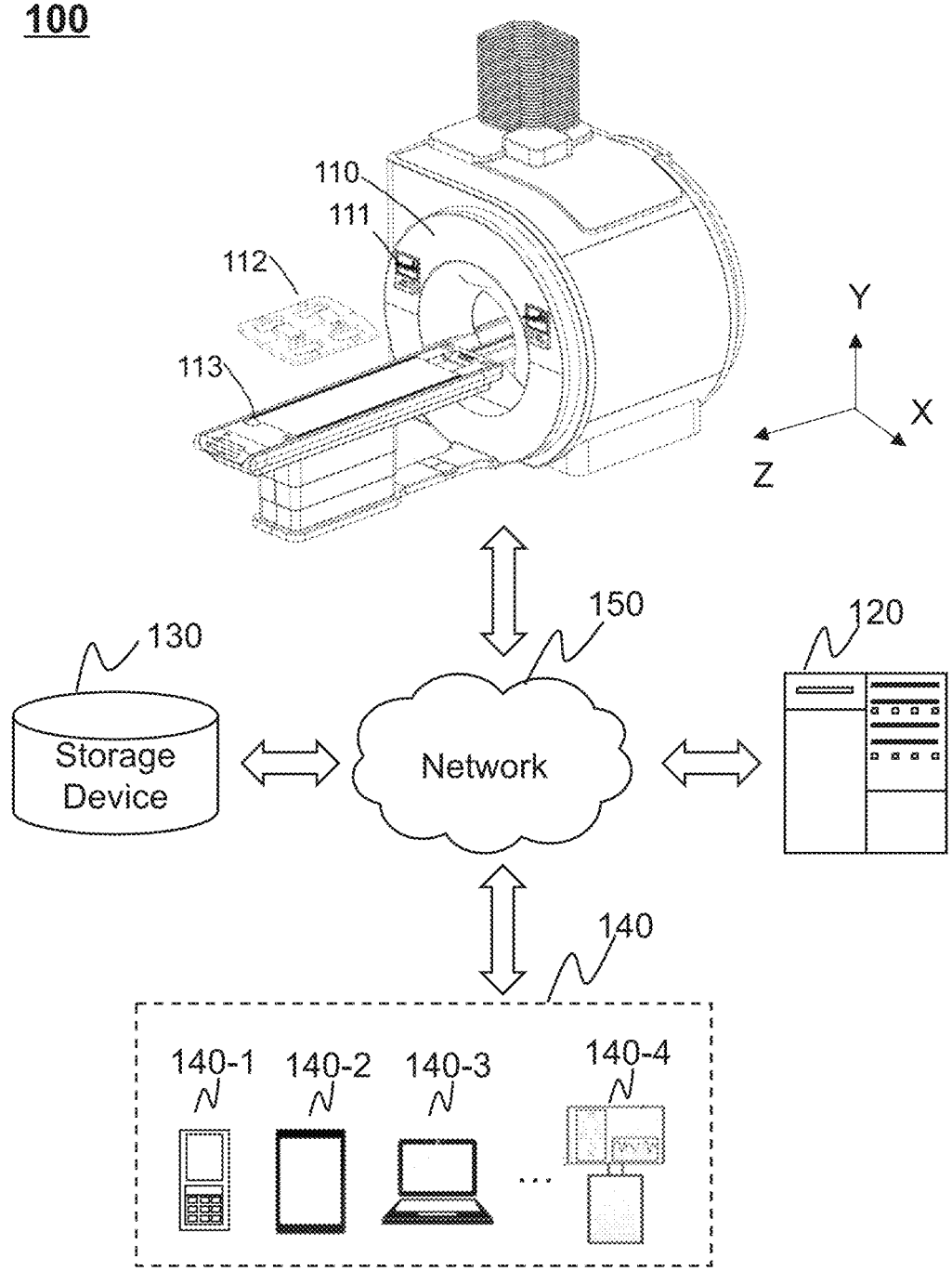
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MRI device 110, a processing device 120, a storage device 130, one or more terminals 140, and a network 150. In some embodiments, the MRI device 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MRI device 110 may be connected to the processing device 120 through the network 150. As another example, the MRI device 110 may be connected to the processing device 120 directly.

The MRI device 110 may be configured to scan a subject (or a part of the subject) to acquire image data, such as MR signals associated with the subject. For example, the MRI device 110 may detect a plurality of MR signals by applying an MR pulse sequence on the subject. In some embodiments, the MRI device 110 may include, for example, a magnetic body, a gradient coil, a display 111, a coil assembly 112, and a table 113, or the like, or any combination thereof. In some embodiments, the MRI device 110 may be a permanent magnet MRI device, a superconducting electromagnet MRI device, or a resistive electromagnet MRI device, etc., according to types of the magnetic body. In some embodiments, the MRI device 110 may be a high-field MRI device, a mid-field MRI device, and a low-field MRI device, etc., according to the intensity of the magnetic field.

The display 111 may be configured to display data and/or information relating to the subject and/or the MRI device 110. For example, the data and/or information may include an operation status of the MRI device 110 (e.g., an operation status of the magnetic body, the gradient coil, and/or the coil assembly 112), information of the subject to be scanned (e.g., height, age, weight, a scanned position), a scanning protocol, a motion signal relating to a physiological motion of the subject, other information relating to the physiological motion (e.g., whether the physiological motion is smooth), or the like, or any combination thereof. In some embodiments, the display 111 may display a motion curve of the subject representing the physiological motion signal of the subject. In some embodiments, the display 111 may include a cathode ray tube (CRT) display, a liquid crystal display (LCD), an organic light emitting display (OLED), a plasma display, or the like, or any combination thereof. In some embodiments, the display 111 may be mounted on the MRI device 110 as shown in FIG. 1. Alternatively, the display 111 may be integrated into a terminal device 140, such as a computer, a laptop, a cell phone, a mobile phone, a pad, a glass, a projector, a virtual reality device, or the like. In some embodiments, the display 111 may be omitted.

In some embodiments, the subject may be placed and supported by the table 113 during a scan of the subject. The table 113 may support and move the subject into/out from a detection tunnel (e.g., a space surrounded by a magnetic body) of the MRI device 110. The subject may be biological or non-biological. For example, the subject may include a patient, a man-made object, etc. As another example, the subject may include a specific portion, organ, tissue, and/or a physical point of the patient. For example, the subject may include head, brain, neck, body, shoulder, arm, thorax, cardiac, stomach, blood vessel, soft tissue, knee, feet, or the like, or a combination thereof. In some embodiments, the subject may be placed on the table 113 in a head first-prone position, a head first-supine position, a head first-decubitus right position, a head first-decubitus left position, a feet first-decubitus right position, a feet first-decubitus left position, a feet first-prone position, a feet first-supine position, or the like.

The coil assembly 112 may be configured to emitted RF signals toward the subject and/or detect MR signals from the subject. In some embodiments, the coil assembly 112 may include an emitting coil configured to emit an RF pulse toward the subject and/or a receiving coil assembly configured to detect MR signals from the subject. In some embodiments, the coil assembly 112 may include one or more sensors configured to detect a motion signal relating to a physiological motion of the subject before and/or during the MR scan. More descriptions regarding the MRI device 110 may be found elsewhere in the present disclosure. See, e.g., FIG. 2 and relevant descriptions thereof.

For illustration purposes, a coordinate system including an X-axis, a Y-axis, and a Z-axis is provided in FIG. 1. The X axis and the Z axis shown in FIG. 1 may be horizontal, and the Y-axis may be vertical. As illustrated, the positive X direction along the X axis may be from the left side to the right side of the MRI device 110 seen from the direction facing the front of the MRI device 110; the positive Y direction along the Y axis shown in FIG. 1 may be from the lower part to the upper part of the MRI device 110; the positive Z direction along the Z-axis shown in FIG. 1 may refer to a direction in which the subject is moved out of the scanning channel (or referred to as the bore) of the MRI device 110.

The processing device 120 may process data and/or information relating to the MRI system 100, such as information obtained from the MRI device 110, the storage device 130, the terminal(s) 140, etc. For example, the processing device 120 may generate an MR image by processing image data (e.g., MR signals) collected by the MRI device 110. As another example, the processing device 120 may determine a motion signal based on information detected by a sensor of the coil assembly 112. In some embodiments, the processing device 120 may be a single server or a server group. The server group may be centralized or distributed. In some embodiments, the processing device 120 may be local or remote. For example, the processing device 120 may access information and/or data from the MRI device 110, the storage device 130, and/or the terminal(s) 140 via the network 150. As another example, the processing device 120 may be directly connected to the MRI device 110, the storage device 130, the terminal(s) 140, or the like, to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MRI device 110, the processing device 120, and/or the terminal(s) 140. For example, the storage device 130 may store MR signals and/or motion signals of the subject received from the coil assembly 112. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MRI device 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MRI device 110 to scan the subject from the user. As another example, the terminal(s) 140 may receive a processing result (e.g., an ECG curve and/or a respiratory signal of the subject) from the processing device 120 and/or the coil assembly 112, and display the processing result to the user. In some embodiments, the terminal(s) 140 may be connected to and/or communicate with the MRI device 110, the processing device 120, and/or the storage device 130. In some embodiments, the terminal(s) 140 may include a mobile device 140-1, a tablet computer 140-2, a laptop computer 140-3, a display device 140-4, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. As another example, the display device 140-4 may include a cathode ray tube (CRT) display, a liquid crystal display (LCD), an organic light emitting display (OLED), a plasma display, or the like, or any combination thereof.

In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MRI device 110.

The network 150 may include any suitable network that can facilitate the exchange of information and/or data for the MRI system 100. In some embodiments, one or more components of the MRI system 100 (e.g., the MRI device 110, the coil assembly 112, the processing device 120, the storage device 130, the terminal(s) 140, etc.) may communicate information and/or data with each other via the network 150. For example, the processing device 120 may obtain image data (e.g., an MR signal) from the MRI device 110 via the network 150. As another example, the processing device 120 may obtain user instructions from the terminal(s) 140 via the network 150. As a further example, the processing device 120 may obtain a motion signal of the subject from the coil assembly 112 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components, such as a control device configured to control the operation of the MRI device 110. The control device may be an independent device of the MRI system 100 or be part of the MRI device 110 or the processing device 120. Additionally or alternatively, one or more components of the MRI system 100 may be omitted or replaced by another device that can realize the same or similar function. In some embodiments, two or more components of the MRI system 100 may be integrated into a single component. Additionally or alternatively, a component of the MRI system 100 may be divided into a plurality of sub-units. However, those variations and modifications do not depart the scope of the present disclosure.

Figure 2:
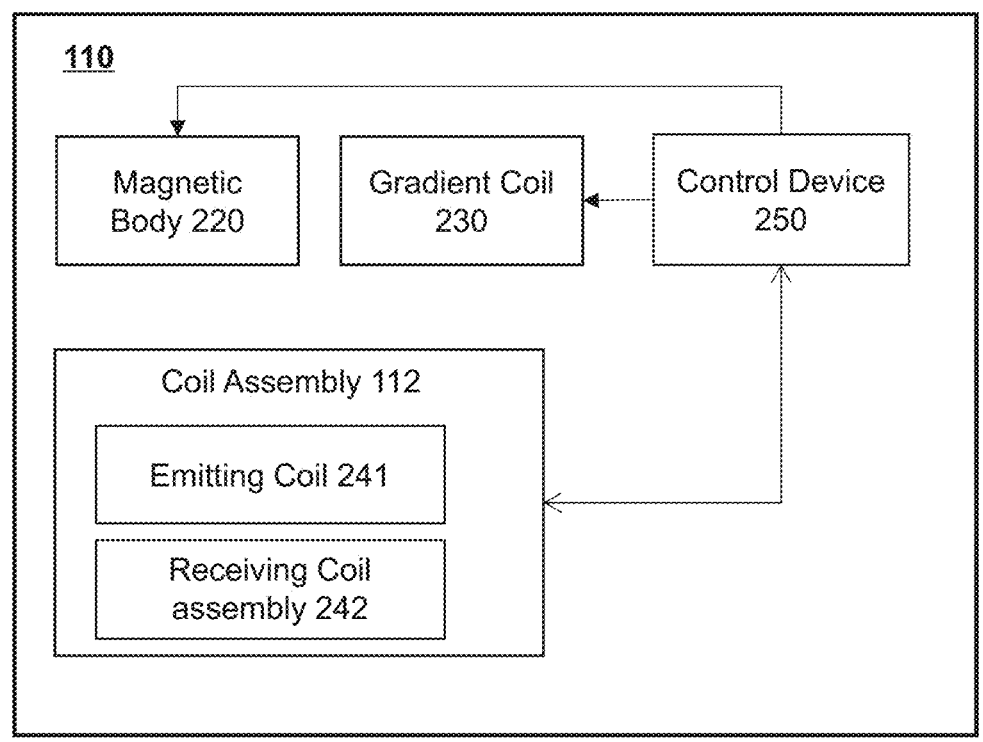
FIG. 2 is a block diagram illustrating an exemplary MRI device according to some embodiments of the present disclosure.

FIG. 2 is a block diagram illustrating an exemplary MRI device 110 according to some embodiments of the present disclosure. As illustrated in FIG. 2, the MRI device 110 may include a magnetic body 220, a gradient coil 230, a coil assembly 112, and a control device 250.

The magnetic body 220 may generate a static magnetic field during the scanning of at least a portion of a subject. The magnetic body 220 may be of various types including, for example, a permanent magnet, a superconducting electromagnet, a resistive electromagnet, etc.

The gradient coil 230 may provide magnetic field gradients to the main magnetic field in an X direction, a Y direction, and/or a Z direction. As used herein, the X direction, the Y direction, and the Z direction may represent an X axis, a Y-axis, and a Z axis in a coordinate system (e.g., a same or similar coordinate system as that described in FIG. 1). For example, the Z-axis may be along the axis of the magnetic body 220, the X axis and the Z axis may form a horizontal plane, and the X axis and the Y axis may form a vertical plane. In some embodiments, the gradient coil 230 may include an X-direction coil for providing a magnetic field gradient to the main magnetic field in the X direction, a Y-direction coil for providing a magnetic field gradient to the main magnetic field in the Y direction, and/or Z-direction coil for providing a magnetic field gradient to the main magnetic field in the Z direction. In some embodiments, the X-direction coil, the Y-direction coil, and/or the Z-direction coil may be of various shape or configuration. For example, the Z-direction coil may be designed based on a circular (Maxwell) coil. As another example, the X-direction coil and the Y-direction coil may be designed on the basis of a saddle (Golay) coil configuration.

The coil assembly 112 may be configured to emitted RF signals toward the subject and/or detect MR signals from the subject. In some embodiments, the coil assembly 112 may include an emitting coil 241 and/or a receiving coil assembly 242. The emitting coil 241 may be configured to emit signals (e.g., RF signals) toward the subject to excite nucleus in the subject to provide a resonation. The receiving coil assembly 242 may receive MR signals emitted from the subject 210 caused by the resonation. In some embodiments, the emitting coil 241 and the receiving coil assembly 242 may be integrated into one same coil. In some embodiments, the coil assembly 112 may be of various types including, for example, a quadrature detection (QD) orthogonal coil, a phased-array coil, a specific element spectrum coil, a birdcage coil, a solenoid coil, a saddle coil, a Helmholtz coil, a loop coil, etc. In some embodiments, the coil assembly 112 may be a volume coil (e.g., a birdcage coil) that can accommodate the entire body of the subject or a local coil (e.g., a loop coil, a solenoid coil) that covers a portion of the subject. In some embodiments, the coil assembly 112 may be a phased-array coil that includes a plurality of coil units, each of which may detect MR signals independently. For example, the coil assembly 112 may be an array coil with a plurality of channels. The count of the channels may be, for example, 4, 8, 16, 24, or 32. In some embodiments, the coil assembly 112 may be placed on a table (e.g., the table 113) of the MRI device 110 or on the body surface of the subject during a scan. For example, during a scan of the heart of the subject, the coil assembly 112 may be placed on the chest of the subject. Optionally, the coil assembly 112 may be attached to the body of the subject via, for example, a strap or tape. As another example, the coil assembly 112 may be placed on the abdomen of the subject configured as a spinal coil placed on the table during a scan of the chest and/or the abdomen of the subject. As yet another example, the coil assembly 112 may be configured as a head coil placed on the table during a scan of the head of the subject.

Figure 11:
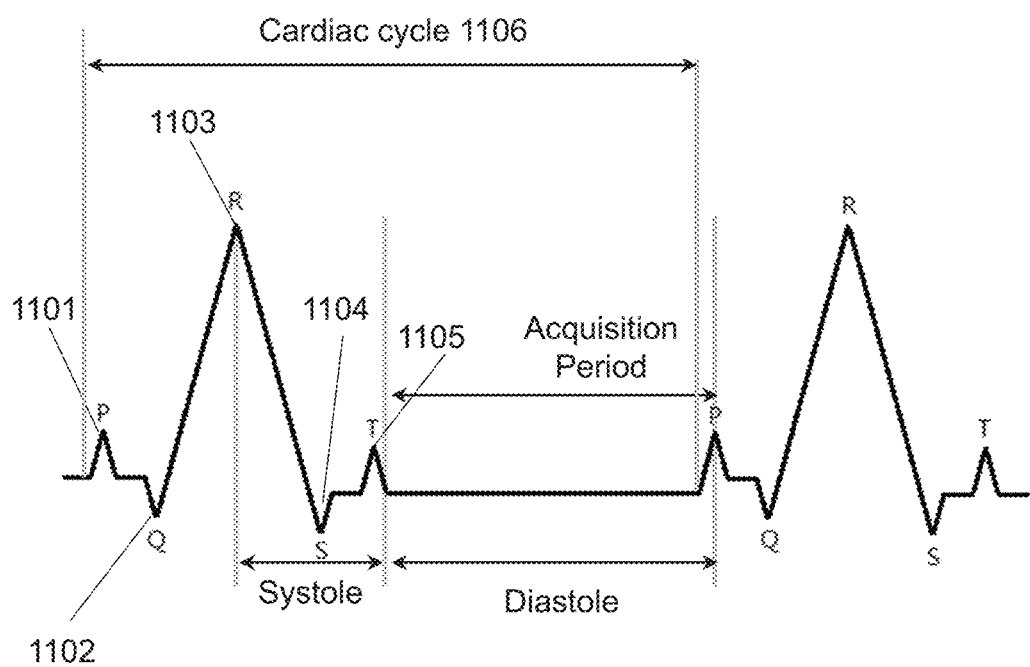
FIG. 11 is a schematic diagram illustrating an exemplary ECG signal curve according to some embodiments of the present disclosure.

In some embodiments, the subject may undergo physiological motion(s), such as a cardiac motion, a respiratory motion, a blood flow, a gastrointestinal motion, a skeletal muscle motion, a brain motion, or the like before and/or during an MR scan. The coil assembly 112 may include one or more sensors (or detectors) configured to detect one or more motion signals, such as an electrocardiogram (ECG) signal relating to the cardiac motion, an electromyography (EMG) signal relating to the skeletal muscle motion, an electroencephalogram (EEG) signal relating to the brain motion, a respiratory signal relating to the respiratory motion, or the like before and/or during the MR scan. As used herein, detecting or determining a motion signal relating to a specific physiological motion of the subject may include determining the motion signal itself (e.g., an ECG signal represented by an ECG curve as indicated in FIG. 11) and/or determining information relating to the signal (e.g., a motion cycle, a motion amplitude, etc.). In some embodiments, the coil assembly 112 may include a respiratory signal detector and/or an ECG sensor. The respiratory signal detector may be used to detect a signal relating to the respiratory motion (also referred to as a respiratory signal) of the subject. The ECG sensor may be used to detect a signal relating to the cardiac motion (also referred to as an ECG signal) of the subject. More descriptions regarding the coil assembly 112 and the sensor(s) may be found elsewhere in the present disclosure. See, e.g., FIG. 5 and relevant descriptions thereof.

The control device 250 may be connected to and/or communicate with one or more components of the MRI system 100 (e.g., one or more other components of the MRI device 110, the processing device 120, the terminal 140, etc.), and configured to control the one or more components. For example, the control device 250 may receive an instruction for scanning (e.g., a scanning protocol) from a terminal 140, and control the MRI device 110 to perform a scan according to the instruction. As another example, as shown in FIG. 2, the control device 250 may be connected to and control the coil assembly 112, the magnetic body 220, and the gradient coil 230. In some embodiments, the coil assembly 112 may transmit a detected motion signal and/or the MR signals to the control device 250. The control device 250 may control one or more components of the MRI device 110, (e.g., the magnetic body 220, the gradient coil 230, the coil assembly 112) according to the motion signal as described elsewhere in this disclosure (e.g., FIG. 13 and the relevant descriptions).

It should be noted that the example in FIG. 2 and the description thereof is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

It is understood that the connections between components of the MRI device 110 in FIG. 2 are illustrative. Any two components of the MRI device 110 may be connected or not. The connection between two components of the MRI device 110 may be a one-way connection or a two-way connection. The connection between two components of the MRI device 110 may include a wired connection and/or a wireless connection. The wired connection may include a metal cable, an optical cable, a hybrid cable, a welding connection (e.g., a soldering connection), or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, the MRI device 110 may include one or more additional components or one or more components described above may be omitted. For example, the control device 250 may be integrated into another component of the MRI system 100, such as the processing device 120. As another example, the control device 250 may be designed as a device independent from the MRI device 110.

FIG. 3 is a schematic diagram illustrating exemplary hardware and/or software components of a computing device 300 according to some embodiments of the present disclosure. In some embodiments, one or more components of the MRI system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage 320, an input/output (I/O) 330, and a communication port 340.

The processor 310 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 310 may process a motion signal of a subject obtained from a coil assembly of an MRI device. The processor 310 may also control the MRI device to perform a scan on the subject according to the motion signal.

In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

The storage 320 may store data/information obtained from the MRI device 110, the terminal(s) 140, the storage device 130, or any other component of the MRI system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to generate a control signal of an MRI device based on a motion signal of a subject scanned or to be scanned by the MRI device.

The I/O 330 may input or output signals, data, or information. In some embodiments, the I/O 330 may enable a user interaction with the processing device 120. In some embodiments, the I/O 330 may include an input device and an output device as described elsewhere in this disclosure (e.g., FIG. 1 and the relevant descriptions).

The communication port 340 may be connected to a network (e.g., the network 150) to facilitate data communications. The communication port 340 may establish connections between the processing device 120 and the MRI device 110, the terminal 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
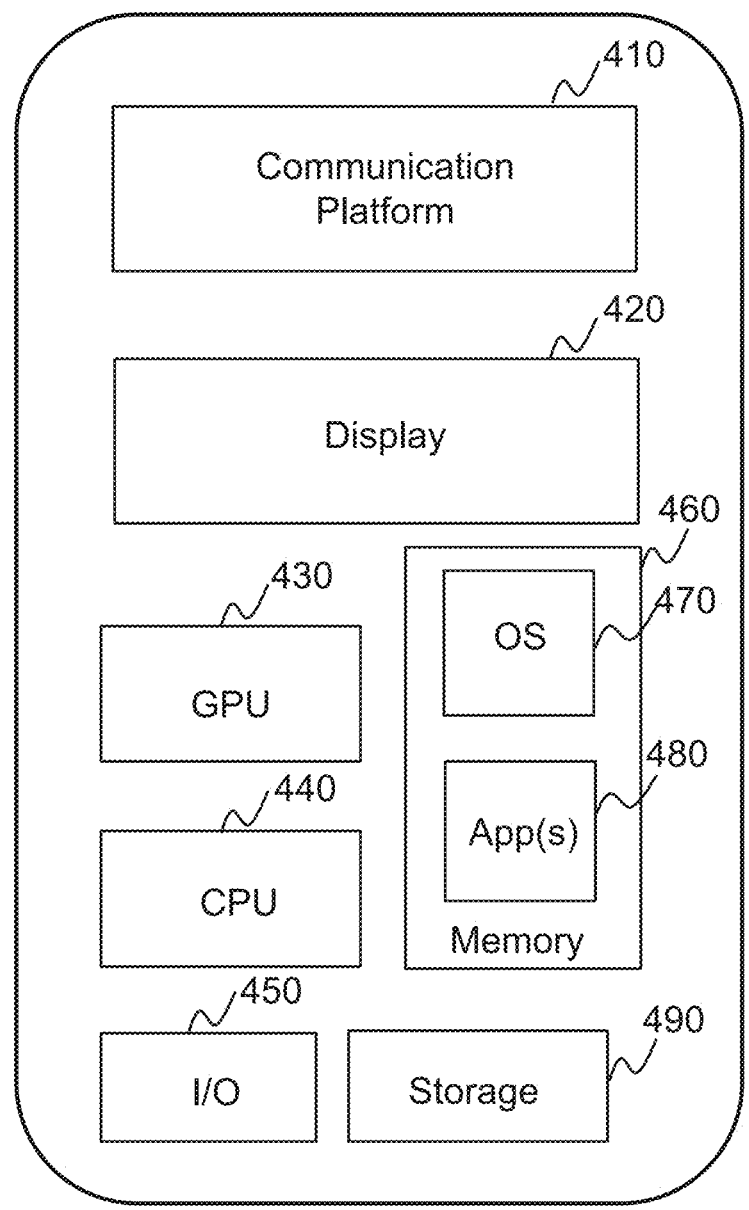
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device according to some embodiments of the present disclosure. In some embodiments, one or more components of the MRI system 100 may be implemented on one or more components of the mobile device 400. Merely by way of example, a terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
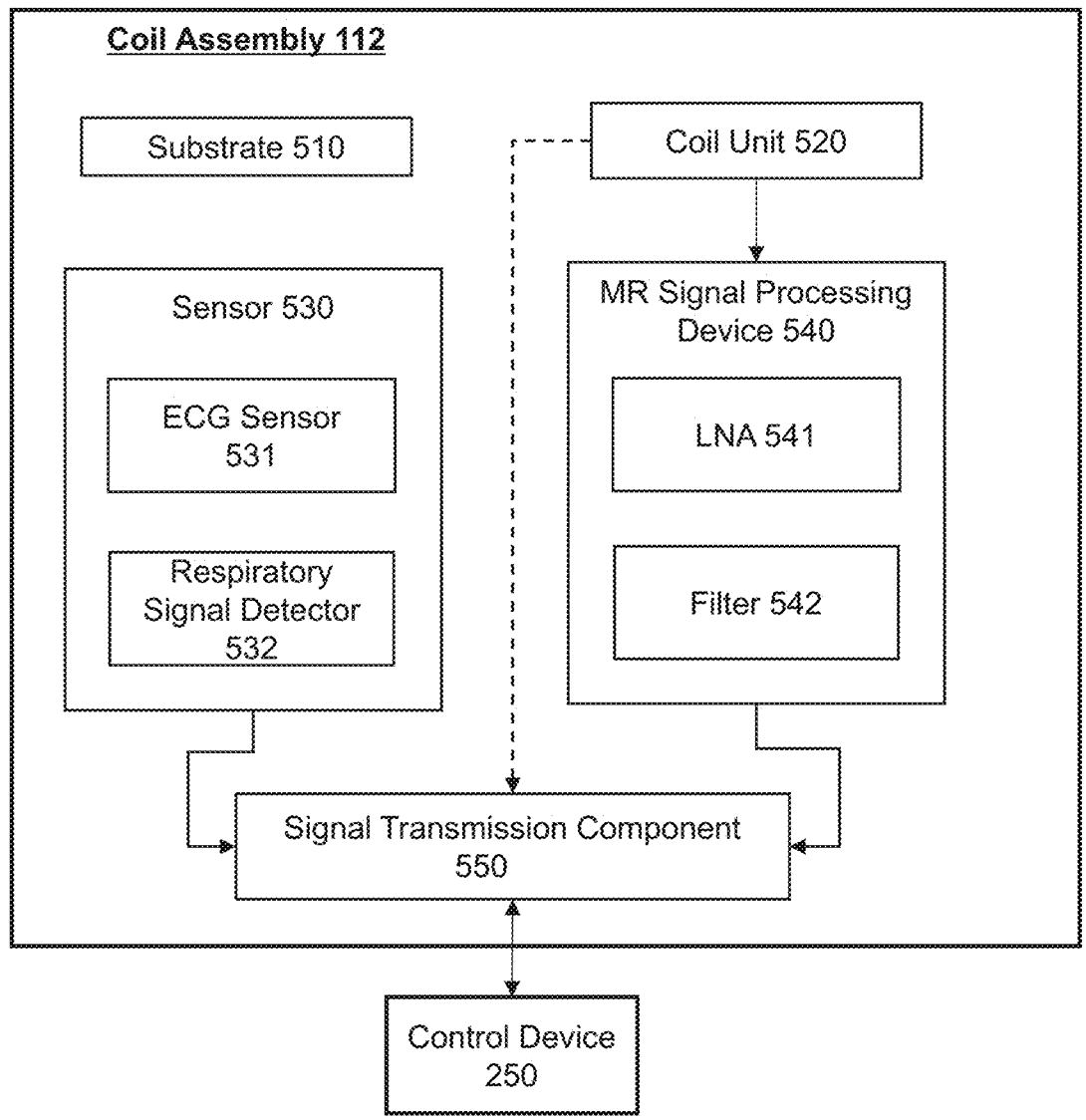
FIG. 5 is a block diagram illustrating an exemplary coil assembly according to some embodiments of the present disclosure.

FIG. 5 is a block diagram illustrating an exemplary coil assembly 112 according to some embodiments of the present disclosure. As shown in FIG. 5, the coil assembly 112 may include a substrate 510, one or more coil units 520, one or more sensors 530, an MR signal processing device 540, and a signal transmission component 550. In some embodiments, during a scan by an MRI device, the coil assembly 112 may be placed on a table of the MRI device or a specific portion of a subject to be scanned as described in connection with FIG. 2.

The substrate 510 may be configured to mount and/or position one or more components of the coil assembly 112. In some embodiments, the substrate 510 may include a single layer. One or more components of the coil assembly 112 (e.g., the coil unit(s) 520 or a portion thereof) may be mounted on the single layer. Alternatively, the substrate 510 may include two or more layers that form one or more chambers. One or more components of the coil assembly 112 may be mounted within a chamber or on an external surface of the substrate 510. Such substrate including two or more layers that forms one or more chambers may be also referred to as a housing.

In some embodiments, the coil unit(s) 520 (or a portion thereof) may be accommodated within the substrate 510, and the substrate 510 may be configured to position the coil unit(s) 520 on the specific portion of the subject to be scanned. Optionally, the coil unit(s) 520 may include a plurality of coil units, which are mounted symmetrically with respect to a midline of the substrate 510. Additionally or alternatively, the sensor(s) 530 may be mounted on or within the substrate 510, and the substrate 510 may be configured to position the sensor(s) 530 on a location to detect a specific motion signal (e.g., near the heart to detect an ECG signal or near the abdomen to detect a respiratory signal).

In some embodiments, the substrate 510 may include a proximal surface and a distal surface opposite to each other. The proximal surface may be close to the subject and the distal surface may be further away, compared to the proximal surface, from the subject during a scan. In some embodiments, a component of the coil assembly 112 may be mounted on an external surface of the substrate 510 and/or within the substrate 510. For example, the coil unit(s) 520 may be mounted within the substrate 510 (e.g., on an internal side of the proximal surface of the substrate 510). As another example, a sensor 530 may be mounted within the substrate 510 or on an external surface of the substrate 510, such as an external surface the proximal surface or the distal surface. As yet another example, the signal transmission component 550 may be mounted on an external surface of the distal surface or the proximal surface. In some embodiments, the sensor(s) 530 may include a plurality of sensors mounted on different positions. For example, a sensor may be mounted on the proximal surface of the substrate 510 and another sensor may be mounted within the substrate 510. As another example, the sensors may both be mounted within the substrate 510.

In some embodiments, the substrate 510 may be made of a flexible material, which is flexible or deformable to fit the scanned subject. Exemplary flexible materials may include plastic, fabric, polyethylene (PE), polypropylene (PP), polyester, ethylene-vinyl acetate (EVA), polybutylene terephthalate (PBT), polycarbonate (PC), polyoxymethylene (POM), polyurethane (PU), polystyrene (PS), nylon, cotton, fiber, resin, or the like, or any combination thereof. Optionally, the substrate 510 may include one or more layers of a flexible material. Alternatively, the substrate 510 may include multiple layers of two or more flexible materials, in which at least two layers include different flexible materials. For example, the substrate 510 may be configured as a bandage which is stretchable, bendable, twistable, and deformable to fit the scanned subject. In some embodiments, the substrate 510 may be made of a nonflexible material which is rigid. The substrate 510 may have any suitable shape and size. In some embodiments, the substrate 510 may include one or more of hollow openings. The one or more hollow openings of the substrate 510 may make the substrate 510 be more flexible and/or deformable to fit the scanned subject. Additionally or alternatively, the one or more hollow openings may be used to dissipate heat generated by the coil assembly 112 and/or reduce the weight of the coil assembly 112.

The coil unit(s) 520 may be configured to receive MR signal(s) from the subject during the scan of the subject. In some embodiments, the coil unit(s) 520 may include a plurality of coil units, each of which may be configured to receive MR signal(s) from the subject during the scan independently or jointly. The coil units may be arranged side by side along at least one direction as described in connection with FIGS. 9A and 9B. In some embodiments, the coil assembly 112 may include an ECG sensor 531. The coil unit(s) 520 may serve as at least a portion of a signal receiver of the ECG sensor 531 as described in connection with FIG. 6. In some embodiments, the coil unit(s) 520 may be made of a flexible conductor material (e.g., copper), a liquid metal, or the like, or any combination thereof. For example, a coil unit may be stretchable and move as an integral piece or relative to another coil unit.

In some embodiments, the coil unit(s) 520 may be operably connected to the MR signal processing device 540. The MR signal(s) received by the coil unit(s) 520 may be transmitted to the MR signal processing device 540 for further processing. For example, the MR signal processing device 540 may process the MR signal(s) by performing a signal amplification, a signal filtering, a signal modulation, a signal demodulation, or the like, or any combination thereof.

The MR signal processing device 540 may include any component that can implement the functions of the MR signal processing device 540. In some embodiments, as illustrated in FIG. 5, the MR signal processing device 540 may include a low noise amplifier (LNA) 541 and a filter 542. The LNA 541 may be configured to amplify the MR signal(s) to generate amplified MR signal(s). In some embodiments, a gain of the LNA 541 may affect a signal-to-noise ratio of the amplified MR signal(s). In order to reduce the signal-to-noise ratio of the amplified MR signal(s), an LNA 541 with a high gain (e.g., a gain higher than a threshold) may be utilized. The filter 542 may be configured to generate the processed MR signal(s) by filtering the amplified MR signal(s). In some embodiments, signals out of a specific frequency band may be filtered by the filter 542 to avoid an interference between signals of different frequency bands.

In some embodiments, the MR signal processing device 540 may be connected to and/or communicate with the signal transmission component 550 as shown in FIG. 5. For example, the MR signal processing device 540 may transmit the processed MR signal(s) to the signal transmission component 550. The signal transmission component 550 may further transmit the processed MR signal(s) to the control device 250. In some embodiments, the MR signal processing device 540 may be omitted, and the coil unit(s) 520 may be directly connected to the signal transmission component 550 as indicated by a dotted arrow in FIG. 5. The MR signal(s) received by the coil unit(s) 520 may be directly transmitted to the control device 250 via the signal transmission component 550 without being processing by the MR signal processing device 540. Alternatively, the signal transmission component 550 may be omitted or integrated into the MR signal processing device 540. The MR signal processing device 540 may be configured to process the MR signal(s) and transmit the processed MR signal(s) to the control device 250.

The sensor(s) 530 may be configured to detect a motion signal relating to a physiological motion of the subject before and/or during the MR scan of the subject. For example, as shown in FIG. 5, the sensor(s) 530 may include an ECG sensor 531 for detecting an ECG signal relating to a cardiac motion of the subject and a respiratory signal detector 532 for detecting a respiratory signal relating to a respiratory motion of the subject.

In some embodiments, a detected motion signal may include information relating to a corresponding physiological motion of the subject. The information relating to a physiological motion may include, for example, a motion rate, a motion amplitude (or displacement), a motion cycle, a motion phase, etc. For example, the ECG signal may indicate cardiac cycle(s) of the subject, as well as changes of heart rate and/or cardiac motion amplitude over the cardiac cycle(s) as shown in FIG. 11. A cardiac cycle may include a plurality of cardiac phases, such as systole (during which the left and right ventricles contract and eject blood into the aorta and pulmonary artery, respectively) and diastole (during which the ventricles are relaxed). As another example, the respiratory signal may indicate a respiratory cycle of the subject, as well as a respiratory displacement, a respiratory rate, and/or a respiratory frequency, etc. The respiratory cycle may include a plurality of respiratory phases, such as an inspiratory phase (during which the chest of the subject expands and air flows into the lungs) and an expiratory phase (during which the chest shrinks and the air is pushed out of the lungs). In some embodiments, a motion cycle (e.g., a cardiac or respiratory cycle) may be used to determine an MR signal acquisition time as described elsewhere in this disclosure (e.g., FIG. 11 and the relevant descriptions).

In some embodiments, the ECG sensor 531 and the respiratory signal detector 532 may be placed at their respective positions during the MR scan of the subject by the substrate 510. For example, the ECG sensor 531 may be placed near the chest of the subject. The respiratory signal detector 532 may be placed on, for example, the chest, the abdomen, or the back of the subject. In some embodiments, the sensor(s) 530 may be actuated during a scan of a specific portion of the subject. For example, the ECG sensor 531 may be actuated to perform its function before and/or during a scan of the chest of the subject. The respiratory signal detector 532 may be actuated to perform its function before and/or during a scan of, for example, the chest, the abdomen, or the back of the subject. In some embodiments, the coil assembly 112 may include two units, one of which includes an ECG sensor 531 and the other of which includes a respiratory signal detector 532. Each unit may include one or more similar components as the coil assembly 112, such as the substrate 510, the coil unit(s) 520, or the like. In some embodiments, one of the ECG sensor 531 and the respiratory signal detector 532 may be omitted.

In some embodiments, the ECG sensor 531 may include a signal emitter, a signal receiver, and a signal processing component. The signal emitter may be configured to emit a reference signal toward the subject, and the reference signal may be reflected by the subject. The signal receiver may be configured to receive at least a portion of the reflected reference signal from the subject. The signal processing component be configured to determine an ECG signal or information relating to the ECG signal by processing the reference signal and/or the received reflected reference signal. More descriptions regarding the ECG sensor 531 may be found elsewhere in the present disclosure. See, e.g., FIG. 6 and relevant descriptions thereof.

In some embodiments, the respiratory signal detector 532 may include a motion sensor configured to detect a respiratory signal and a pad configured to accommodate the motion sensor. Exemplary motion sensors of the respiratory signal detector 532 may include a pressure sensor, an accelerometer sensor, a speed sensor, a gravity sensor, or any sensor that can detect the respiratory signal of the subject. In some embodiments, the respiratory signal detector 532 may include a pressure sensor and a pressure pad. The pressure sensor may be mounted within the pressure pad. The pressure pad may be placed on, for example, the chest, the abdomen, and/or the back of the subject. The pressure sensor may detect a pressure change of the chest, the abdomen, and/or the back of the subject caused by the respiratory motion of the subject. The pressure sensor or another processing device may generate the respiratory signal by processing the pressure change. In some embodiments, the respiratory signal detector 532 may be mounted on the proximal surface of the substrate 510 (e.g., a center position of the proximal surface).

In some embodiments, the sensor(s) 530 may be directly connected to and/or communication with one or more components of the MRI system 100. Additionally or alternatively, the sensor(s) 530 may be operably connected to the signal transmission component 550 and communicate with one or more components of the MRI system 100 via the signal transmission component 550. For example, the motion signal(s) detected by the sensor(s) 530 may be transmitted to the control device 250 via the signal transmission component 550. In some embodiments, the motion signal(s) may be analyzed by one or more components of the MRI system 100 (e.g., the sensor(s) 530 itself, the processing device 120, a signal processing component described hereinafter) to guide the operation of the MRI device 110. For example, based on a motion signal, an MR signal acquisition time for the MRI device 110 to perform the MR scan may be determined. As yet another example, if a motion signal acquired during an MR scan indicates that the physiological motion of the subject is not smooth, the MRI device 110 may be caused to pause or terminate the MR scan. More descriptions regarding the analysis of the motion signal(s) may be found elsewhere in the present disclosure. See, e.g., FIG. 13 and relevant descriptions thereof.

The signal transmission component 550 may be configured to establish connection(s) between a component of the coil assembly 112 and one or more components of the MRI system 100, such as the control device 250, the processing device 120. For example, the signal transmission component 550 may establish a connection between the control device 250 and the sensor(s) 530, and a connection between the control device 250 and the MR signal processing device 540 as shown in FIG. 5. In some embodiments, the signal transmission component 550 may include a communication port (e.g., the communication port 340) to establish a wired connection and/or a wireless connection between two components. Additionally or alternatively, the signal transmission component 550 may include one or more signal processing components (such as a wave trap, an amplifier, a filter, a processor) configured to process a signal to be transmitted.

It should be noted that the example in FIG. 5 and the above description thereof is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, one or more components of the coil assembly 112 may be omitted or be replaced by one or more components that can realize same or similar functions. For example, the filter 542 of the MR signal processing device 540 may be omitted. Additionally or alternatively, the coil assembly 112 may further include one or more additional components. For example, the coil assembly 112 may include one or more signal transmission components. Merely by way of example, the coil assembly 112 may include two signal transmission components, one of which is used to transmit the motion signal(s) detected by the sensor(s) 530, and the other of which is used to transmit the MR signal(s) received by the coil unit 520. As another example, the coil assembly 112 may include a circuit mounted within the substrate 510. One or more components (e.g., the coil unit(s) 520, the sensor 530, etc.) of the coil assembly 112 may be mounted on the circuit board.

In some embodiments, two or more components of the coil assembly 112 may be integrated into one component. For example, the MR signal processing device 540 may be integrated with the signal transmission component 550. In some embodiments, the connections between components of the coil assembly 112 may be variable. Any two components of the coil assembly 112 may be connected or not, and a connection between two components may be a one-way connection or a two-way connection.

Figure 6:
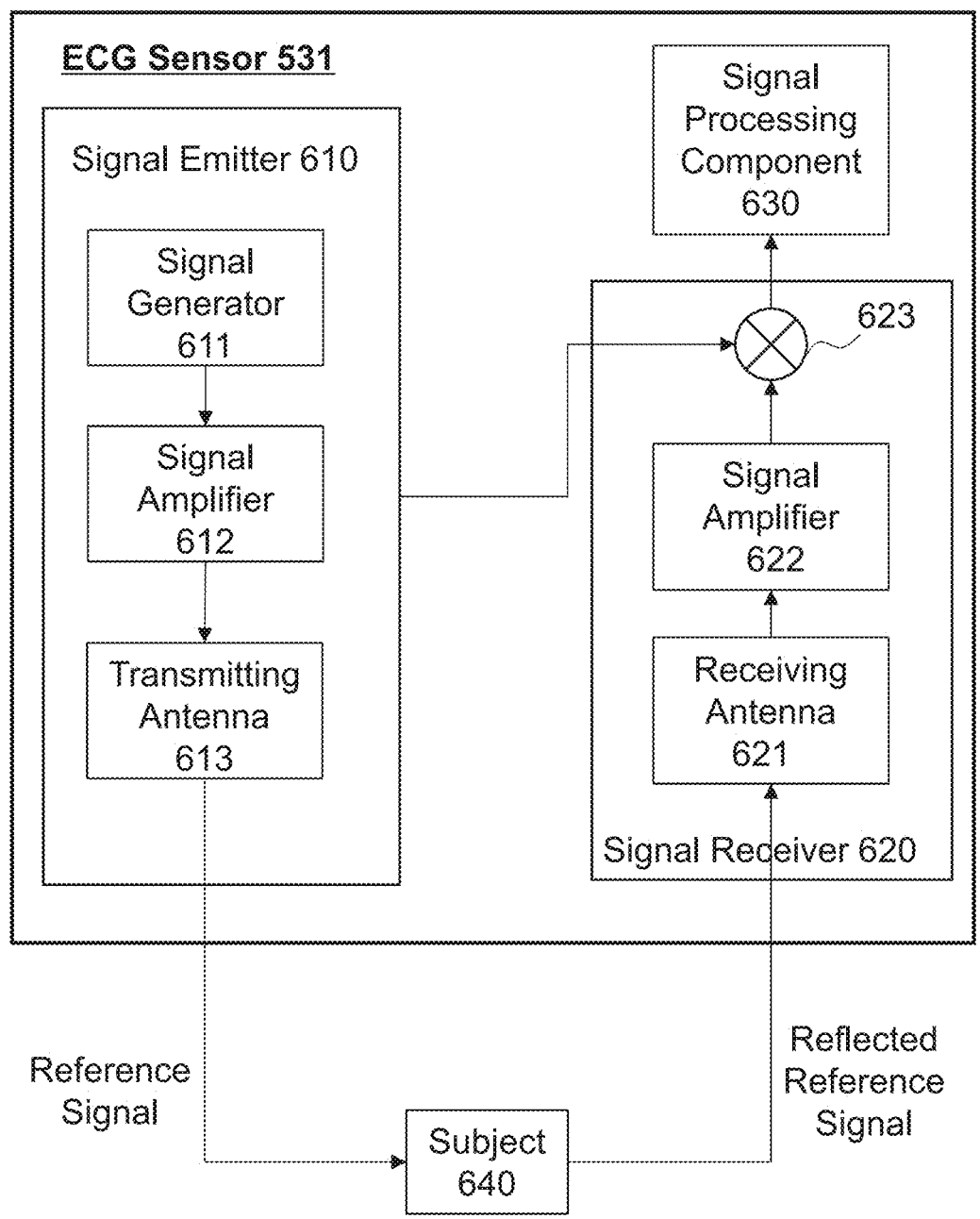
FIG. 6 is a block diagram illustrating an exemplary ECG sensor according to some embodiments of the present disclosure.

FIG. 6 is a block diagram illustrating an exemplary ECG sensor 531 according to some embodiments of the present disclosure. The ECG sensor 531 may be configured to determine an ECG signal and/or information relating to the ECG signal of a subject 640 before and/or during an MR scan of the subject 640. As shown in FIG. 6, the ECG sensor 531 may include a signal emitter 610, a signal receiver 620, and a signal processing component 630.

Figure 10:
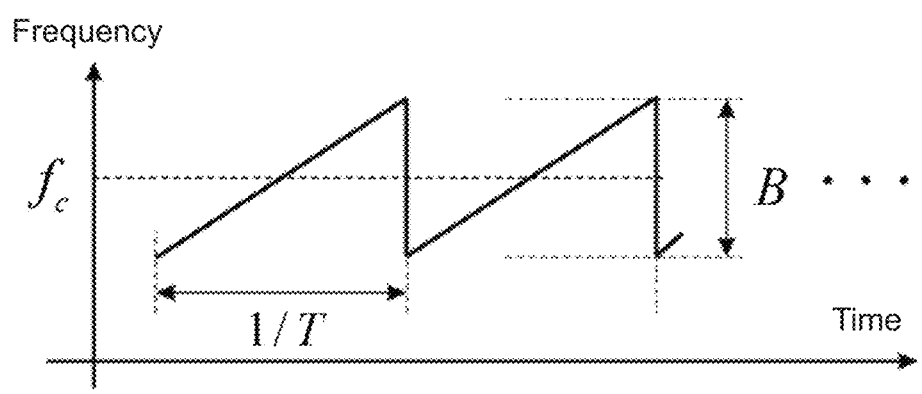
FIG. 10 is a schematic diagram illustrating an exemplary reference signal curve according to some embodiments of the present disclosure.

The signal emitter 610 may be configured to emit a reference signal toward the subject 640 or a portion of the subject 640 (e.g., the chest of the subject 640). In some embodiments, the reference signal may be a radio-frequency (RF) signal, a continuous wave, a pulse signal, or the like. In some embodiments, the frequency of the reference signal may be greater than a threshold frequency (e.g., 1 GHz, 2 GHz, 3 GHz, 5 GHz, 10 GHz, 15 GHz, etc.). In some embodiments, the reference signal may be a continuous wave signal with a time-varying frequency. For example, the frequency of the reference signal may have a linear change or a stepping change over time. For illustration purposes, FIG. 10 illustrates a frequency curve of an exemplary reference signal 1000 according to some embodiments in the present disclosure. As shown in FIG. 10, the reference signal 1000 is a continuous wave including a plurality of signal cycles with a frequency band B and a center frequency $f_c$. The reference signal 1000 may have a repetition period T and the frequency of the reference signal 1000 changes linearly in each signal cycle.

In some embodiments, the signal emitter 610 may include any component that can emit the reference signal. For example, as illustrated in FIG. 6, the signal emitter 610 may include a signal generator 611, a signal amplifier 612, and a transmitting antenna 613. The signal generator 611 may be configured to generate a preliminary reference signal and transmit the preliminary reference signal to the signal amplifier 612. The signal amplifier 612 may be configured to generate the reference signal by amplifying the preliminary reference signal. The reference signal may be transmitted from the signal amplifier 612 to the transmitting antenna 613, and the transmitting antenna 613 may be configured to emit the reference signal toward the subject 640. The transmitting antenna 613 may include a resonant antenna, a non-resonant antenna, or any other type of antenna. In some embodiments, the signal emitter 610 may be connected to a signal mixer 623 of the signal receiver 620 and transmit the reference signal to the signal mixer 623.

In some embodiments, one or more components of the signal emitter 610 may be omitted. For example, the signal amplifier 612 may be omitted. The preliminary reference signal emitted by the signal generator 611 may serve as the reference signal and be transmitted toward the subject 640 via the transmitting antenna 613 directly.

The reference signal emitted toward the subject 640 may be reflected by the subject 640. The signal receiver 620 may be configured to receive at least a portion of the reflected reference signal. In some embodiments, the signal receiver 620 (or a portion thereof) may be integrated into coil unit(s) (e.g., the coil unit(s) 520) of an MRI device. The frequency of the reference signal and/or the reflected reference signal may be associated with the center frequency of the MRI device (e.g., 64 MHz for a 1.5 T MRI device, 128 MHz for a 3.0 T MRI device). For example, the operation frequency of the coil unit(s) may be equal to or substantially equal to the center frequency of the MRI device. The frequency of the reference signal and/or the reflected reference signal may be different from the center frequency but within a frequency band that can be received by the coil unit(s). In this way, the reflected reference signal may be able to be received by the coil unit(s) and distinguished from MR signals according to their respective frequencies. In some embodiments, the difference between the center frequency of the MRI device and the frequency of the reflected reference signal (or the reference signal) may be smaller than a threshold frequency, such as 0.5 Hz, 1 Hz, or 2 Hz. In some embodiments, the reflected reference signal may have a same frequency as the reference signal but a different phase compared with the reference signal. The phase difference between the reflected reference signal and the reference signal may reflect a cardiac motion of the subject 640, and be used to determine the ECG signal of the subject 640.

In some embodiments, the signal receiver 620 may include any component that can receive at least a portion of the reference signal reflected from the subject 640. As illustrated in FIG. 6, the signal receiver 620 may include a receiving antenna 621, a signal amplifier 622, and a signal mixer 623. The receiving antenna 621 may be configured to receive at least a portion of the reflected reference signal from the subject 640 and transmit the received reflected reference signal to the signal amplifier 622. The receiving antenna 621 may include a resonant receiving antenna, a non-resonant receiving antenna, or an antenna of another type. In some embodiments, the frequency of the received reference signal may be within a frequency band that can be received by the receiving antenna 621.

The signal amplifier 622 may be configured to amplify the received portion of the reflected reference signal and transmit the amplified portion of the reflected reference signal to the signal mixer 623. The signal mixer 623 may be configured to generate a mixed signal by mixing the reference signal emitted by the signal emitter 610 with the amplified portion of the reflected reference signal. The mixed signal may include information relating to the cardiac motion of the subject 640. In some embodiments, the signal mixer 623 may be operably connected to the signal processing component 630 and transmit the mixed signal to the signal processing component 630 for further processing.

The signal processing component 630 may be configured to determine the ECG signal relating to the cardiac motion of the subject based on the mixed signal. For example, the signal processing component 630 may generate an ECG curve representing the ECG signal and/or determine information relating to the cardiac motion of the subject 640, such as a cardiac cycle, a heartbeat rate (or a change of the heartbeat rate), a motion amplitude, etc. As another example, the signal processing component 630 may determine a smooth period of the cardiac motion (e.g., diastole or a portion of the diastole) according to the ECG signal. More descriptions regarding the smooth period of the cardiac motion may be found elsewhere in the present disclosure. See, e.g., FIG. 11 and relevant descriptions thereof.

In some embodiments, the determined ECG signal may relate to a specific physical point of the heart of the subject 640. For example, an ECG curve indicating a motion amplitude of the specific physical point at different times may be generated. Merely by way of example, assuming that the signal emitter 610 may emit a reference signal $s_T(t)$ in a time cycle represented by Equation (1) below:

$$s_T(t) = \exp\left(j\left(2\pi f_c t + \pi \frac{B}{T} t^2 + \phi\right)\right), \quad (1)$$

where t represents a fast-time (i.e., a period between a time point when the signal emitter 610 emits the reference signal and a time point when the signal receiver 620 receives at least a portion of the reflected reference signal is received by); $f_c$ represents a center frequency of the reference signal; T represents a repetition period of the frequency of the reference signal; B represents a frequency band of the reference signal; B/T represents a slop of a frequency change of the reference signal; and $\phi$ represents a preliminary phase of the reference signal.

The subject 640 may undergo a cardiac motion before and/or during an MR scan. A distance from a specific physical point on the heart of the subject 640 to the signal receiver 620 (e.g., the receiving antenna 621) may vary with a slow-time $\tau$ and be denoted as $R(\tau)$. The distance $R(\tau)$ may indicate the position and/or the motion amplitude of the specific physical point at different times. A reflected reference signal $S_R(t)$ of the reference signal $s_T(t)$ may be represented by Equation (2) below:

$$S_R(t) = \sigma S_T\left(t - \frac{2R(\tau)}{c}\right), \quad (2)$$

where c represents the velocity of light and $\sigma$ represents a constant parameter. A mixed signal $S_m(t)$ may be generated by mixing the reference signal $s_T(t)$ and the reflected reference signal $S_R(t)$. The mixed signal $S_m(t)$ may be represented by Equation (3) below:

$$S_m(t) = s_T(t) S_R^*(t) = \sigma \exp\left(j\left(\frac{4\pi B R(\tau) t}{cT} + \frac{4\pi f_c R(\tau)}{c} + \phi_2\right)\right), \quad (3)$$

where $S_R^*(t)$ represents a conjugated signal of the reflected reference signal $S_R(t)$, and $\phi_2$ represents a phase difference.

In some embodiments, a frequency $f_b$ of an ECG signal at the specific physical point, which changes with time, may be determined based on the mixed signal $S_m(t)$. For example, the frequency $f_b$ may be determined by filtering the mixed signal $S_m(t)$. The $R(\tau)$ of the specific physical point may be further determined according to Equation (4) below:

$$f_b = \frac{2BR(\tau)}{cT}. \quad (4)$$

In some embodiments, for a plurality of physical points on the heart of the subject 640, the signal processing component 630 may determine an ECG signal relating to each physical point. Optionally, the signal processing component 630 may determine an ECG signal relating to the whole heart based on the ECG signal relating to each of the physical points. In some embodiments, the signal processing component 630 may be operably connected to one or more components of the MRI system 100 (e.g., the control device 250) via the signal transmission component 550 or directly. Optionally, the signal processing component 630 may transmit a processing result or an intermediate result to a component connected to the signal processing component 630. For example, the determined ECG signal of the subject 640 may be transmitted to a processing device (e.g., the processing device 120). The processing device may control the MRI device according to the ECG signal directly or via the control device 250. In some embodiments, the signal processing component 630 may be omitted or integrated into another processing device (e.g., the processing device 120). The functions of the signal processing component 630 may be implemented by the processing device. In some embodiments, the functions of the signal processing component 630 may be implemented by the signal processing component 630 and another processing device (e.g., the processing device 120) jointly or separately.

It should be noted that the example illustrated in FIG. 6 and the above descriptions thereof are intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. In some embodiments, the ECG sensor 531 may include one or more additional components and/or one or more components of the ECG sensor 531 described above may be omitted. For example, the signal amplifier 622 and/or the signal processing component 630 may be omitted. In some embodiments, a component of the ECG sensor 531 may be integrated with another component of the ECG sensor 531 or another device of the MRI system 100. For example, the receiving antenna 621 and the signal amplifier 622 may be integrated into a signal component used to receive and amplify at least a portion of the reflected reference signal. As another example, at least a portion of the signal receiver 620 (e.g., the signal amplifier 622, the signal mixer 623) may be integrated into the coil unit(s). The integrated coil unit(s) may be configured to receive both MR signals and at least a portion of the reflected reference signal. As yet another example, the signal amplifier 622 and/or the signal mixer 623 may be integrated into the signal processing component 630. In some embodiments, an amplifier described herein may incorporate therein a filter to improve signal transmission quality by filtering a signal to be amplified by the amplifier or an amplified signal generated by the amplifier.

Figure 7A:
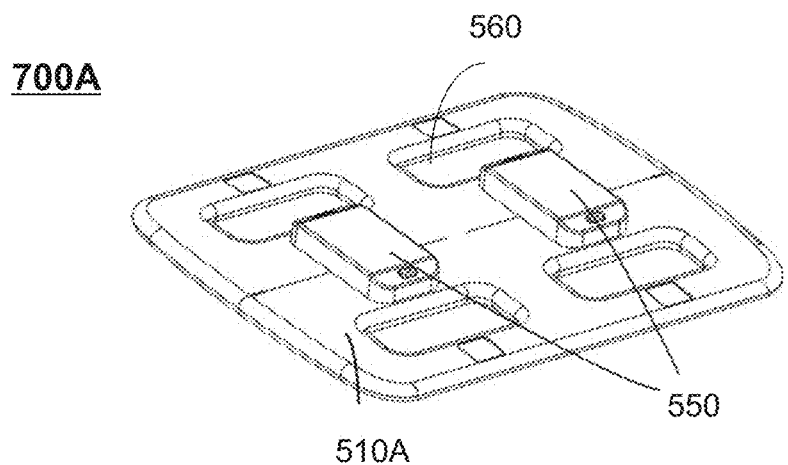
FIGS. 7A to 7D are schematic diagrams illustrating exemplary coil assemblies according to some embodiments of the present disclosure.
Figure 7B:
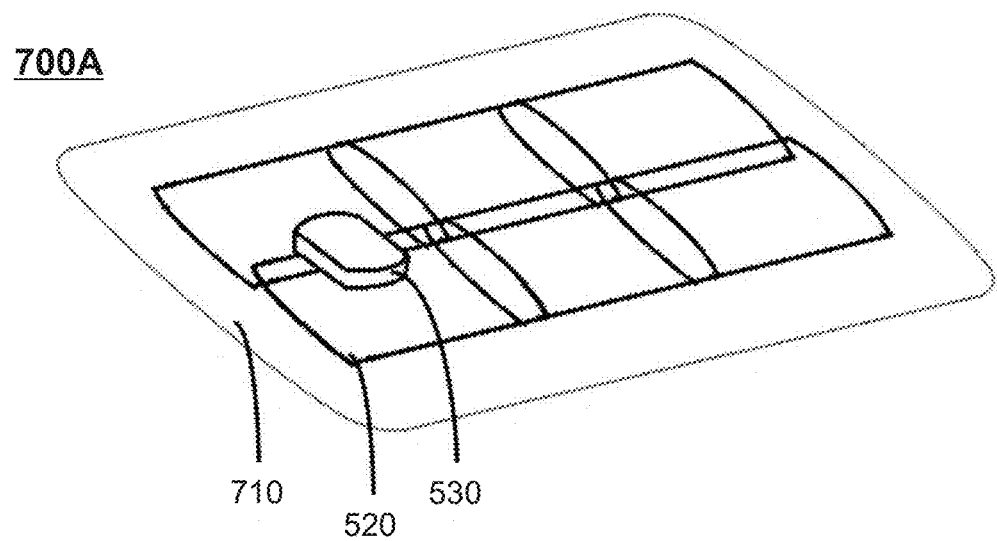

FIGS. 7A and 7B are schematic diagrams illustrating an exemplary coil assembly 700A according to some embodiments of the present disclosure. The coil assembly 700A is an exemplary embodiment of the coil assembly 112 as described elsewhere in this disclosure (e.g., FIGS. 2 and 5 and the relevant descriptions).

The coil assembly 700A may include a substrate 510A. FIG. 7A illustrates the substrate 510A and components of the coil assembly 700A outside the substrate 510A. FIG. 7B illustrates components of the coil assembly 700A inside the substrate 510A. As shown in FIG. 7A, the coil assembly 700A includes two signal transmission components 550 mounted on an external surface of the substrate 510A. The substrate 510A includes a plurality of hollow openings 560.

As shown in FIG. 7B, a sensor 530 for detecting a motion signal, a plurality of coil units 520, and a circuit board 710 are accommodated in the substrate 510A. In some embodiments, the coil units 520 and/or the sensor 530 may be mounted on the circuit board 710 via a mounting mechanism, such as a glue or an adhesive (e.g., an epoxy structural adhesive, an acrylic structural adhesive, a silicone structural adhesive, or the like, or any combination thereof). Alternatively, the coil units 520 and/or the sensor 530 may be integrated into the circuit board 710. In some embodiments, the sensor 530 may include a signal emitter (e.g., the signal emitter 610) and a signal receiver (e.g., the signal receiver 620). Optionally, the signal receiver (or a portion thereof) may be integrated into the coil units 520. In some embodiments, the coil units 520 and the sensor 530 may share a power supply, or be provided with an independent power supply, respectively. In some embodiments, the circuit board 710 may include one or more hollow openings.

In some embodiments, each of the signal transmission components 550 may establish a connection between a component of the coil assembly 700A and another component of the MRI system 100 (e.g., the control device 250). For example, one of the signal transmission components 550 may be operably connected to the sensor 530 for transmitting the motion signal detected by the sensor 530, and the other one may be operably connected to the coil units 520 for transmitting the MR signals detected by the coil units 520. In some embodiments, the coil assembly 700A may include a predetermined count of signal transmission components 550. Alternatively, the count of the signal transmission components 550 may be determined based on actual needs. For example, the count of the signal transmission components 550 may be determined based on an arrangement of the coil units 520, for example, more signal transmission components 550 may be needed if the size of coil units 520 exceeds a threshold size in order to improve the signal transmission quality. In some embodiments, the signal transmission components 550 may be mounted on any position of the coil assembly 700A. For example, a signal transmission component 550 may be mounted on an external surface of the substrate 510A, so that heat generated by the signal transmission component 550 can easily be dissipated without affecting the operation of the coil assembly 700A.

Figure 7C:
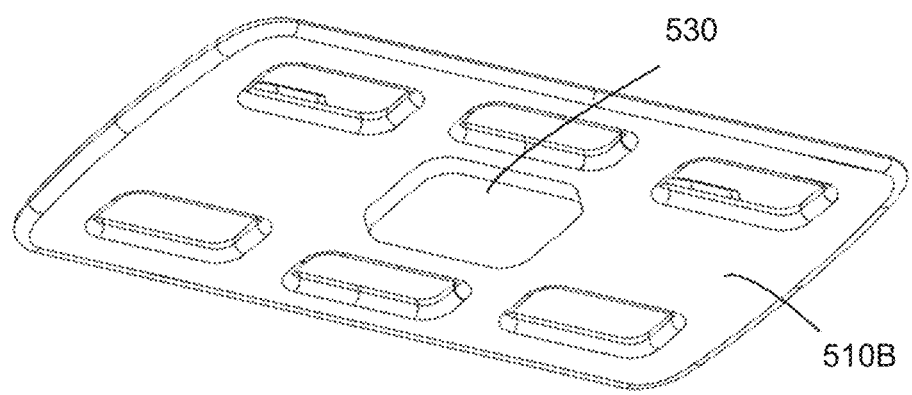
Figure 7D:
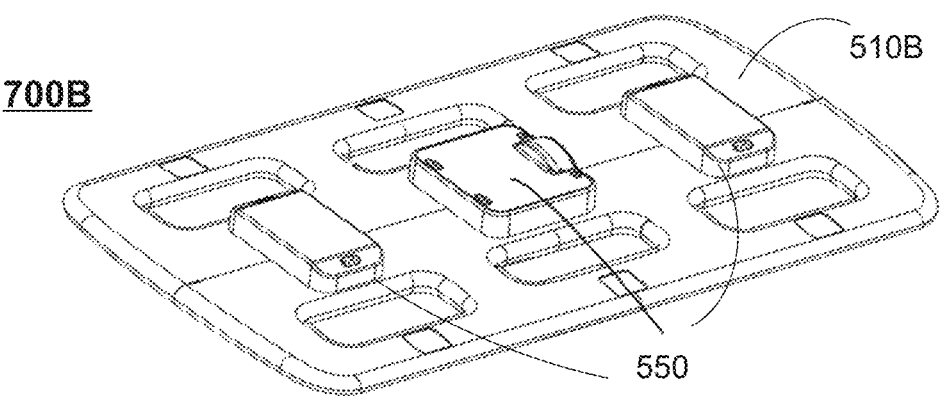

FIGS. 7C and 7D are schematic diagrams illustrating an exemplary coil assembly 700B according to some embodiments of the present disclosure. The coil assembly 700B may be similar to the coil assembly 700A, except for certain components or features. As shown in FIGS. 7C and 7D, the coil assembly 700B includes a substrate 510B, a sensor 530, and three signal transmission components 550. The substrate 510B has more hollow openings than the substrate 510A of the coil assembly 700A. The sensor 530 of the coil assembly 700B is mounted on a first surface of the coil assembly 700B as shown in FIG. 7C. The signal transmission components 550 of the coil assembly 700B are mounted on a second surface opposite to the first surface of the coil assembly 700B as shown in FIG. 7D. In some embodiments, in operation, the first surface may be close to a subject to be scanned, and the second surface may be spaced further apart from the subject compared to the first surface.

Figure 8A:
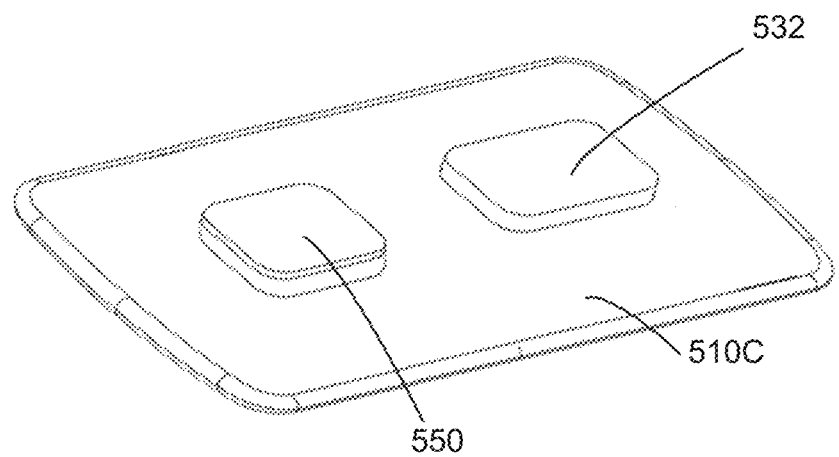
FIGS. 8A to 8B are schematic diagrams illustrating exemplary coil assemblies according to some embodiments of the present disclosure.
Figure 8B:
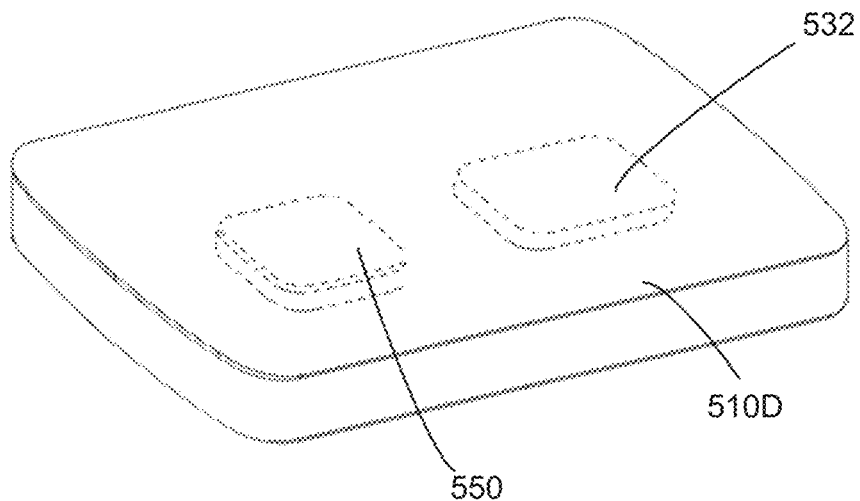

FIGS. 8A and 8B are schematic diagrams illustrating exemplary coil assemblies 800A and 800B according to some embodiments of the present disclosure. The coil assemblies 800A and 800B are exemplary embodiments of the coil assembly 112. Each of the coil assemblies 800A and 800B includes a respiratory signal detector 532 and a signal transmission component 550.

As shown in FIG. 8A, the coil assembly 800A further includes a substrate 510C. The respiratory signal detector 532 and the signal transmission component 550 of the coil assembly 800A are both mounted on an external surface of the substrate 510C. As shown in FIG. 8B, the coil assembly 800B further includes a substrate 510D. The substrate 510D has a relatively larger thickness than the substrate 510C. The respiratory signal detector 532 and the signal transmission component 550 of the coil assembly 800B are both mounted within the substrate 510D.

It should be noted that the examples in FIG. 7A to 8B are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the shape, size, and position of a component illustrated in figures are illustrative and can be modified. Merely by way of example, in the coil assembly 800B, the signal transmission component 550 may be mounted on an external surface of the substrate 510D.

Figure 9A:
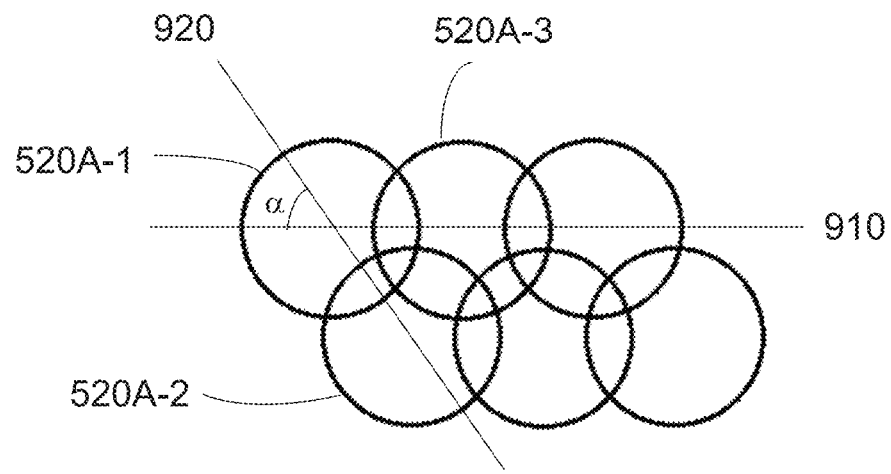
FIG. 9A is a schematic diagram illustrating an exemplary arrangement of coil units according to some embodiments of the present disclosure.

FIG. 9A is a schematic diagram illustrating an exemplary arrangement of coil units 520A according to some embodiments of the present disclosure. The coil units 520A are exemplary embodiments of the coil unit(s) 520 as described in connection with FIG. 5. As shown in FIG. 9A, the coil units 520A include six coil units (e.g., coil units 520A-1, 520A-2, and 520A-3), which are arranged in two rows along a first direction indicated by a line 910 and three columns along a second direction indicated by a line 920. The first direction and the second direction may form an angle α that is greater than 0 degree and smaller than 90 degrees as shown in FIG. 9A. In some embodiments, two adjacent coil units 520A may overlap. For example, the coil unit 520A-1 may partially overlap the coil unit 520A-3 along the first direction, and partially overlap the coil unit 520A-2 along the second direction as shown in FIG. 9A. In some embodiments, one or more decoupling techniques, such as an overlapping decoupling, a capacitive decoupling, an inductor decoupling, or the like may be utilized to eliminate or reduce coupling between adjacent overlapping coil units.

Figure 9B:
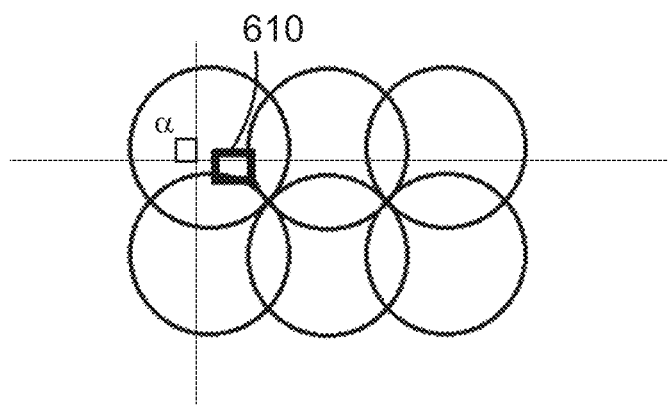
FIG. 9B is a schematic diagram illustrating another exemplary arrangement of coil units according to some embodiments of the present disclosure.

FIG. 9B is a schematic diagram illustrating an exemplary arrangement of coil units 520B according to some embodiments of the present disclosure. The coil units 520B may be arranged in a similar manner as the coil unit 520A, except that the first direction along which a row of coil units 520B are arranged and the second direction along which a column of coil units 520B are arranged are perpendicular to each other as shown in FIG. 9B. In some embodiments, a signal emitter 610 of an ECG sensor (not shown in FIG. 9B) may be mounted on the left portion of the coil units 520B (e.g., a portion which is adjacent to the heart of a subject during a scan) as illustrated in FIG. 9B. The coil units 520B (or a portion thereof) may serve as a signal receiver of the ECG sensor. For example, the signal emitter 610 may emit a reference signal toward a subject, and the coil units 520B may be used to receive at least a portion of a reflected reference signal reflected by the subject. By using the coil units 520B as the signal receiver may reduce the system complexity and improve the utilization of the coil units 520B.

It should be noted that the examples in FIG. 9A to 9B are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the shape, size, and arrangement of the coil units illustrated in figures are illustrative and can be modified. In some embodiments, the coil units may be arranged in any number of columns and/or any number of rows. The angle between the first direction and the second direction may have any degree greater than 0 degrees and smaller than 360 degrees. Two adjacent coil units may at least partially overlap with each other or not overlap at all.

FIG. 11 is a schematic diagram illustrating an exemplary ECG signal curve 1100 according to some embodiments of the present disclosure. The ECG signal curve 1100 may include one or more cardiac cycles. As shown in FIG. 11, a cardiac cycle 1106 includes a P-wave 1101 representing atrial depolarization, a QRS complex representing ventricular depolarization, and a T-wave 1105 representing ventricular repolarization. The QRS complex may include a Q-wave 1102, an R-wave 1103, and an S-wave 1104. The cardiac cycle 1106 begins with the P-wave 1101 and ends by a P-wave of a next cardiac cycle.

In some embodiments, the cardiac cycle 1106 may include a plurality of motion phases, e.g., systole and diastole as shown in FIG. 11. The systole may refer to a period from the beginning of the R-wave to the end of the T-wave, and the diastole may refer to a period from the end of the T-wave to the P-wave of the next cardiac cycle. Normally, during the diastole, the heart remains stationary or substantially stationary. The diastole or a portion of the diastole (e.g., a mid-later period in the diastole) may be regarded as a smooth period of cardiac motion. Optionally, the smooth period may serve as an MR signal acquisition period because that MR signals acquired in this period may be less affected by cardiac motion and have higher signal quality compared with MR signals acquired in other periods (e.g., the systole). This may reduce cardiac motion-induced artifacts in a resulting image.

Figure 12:
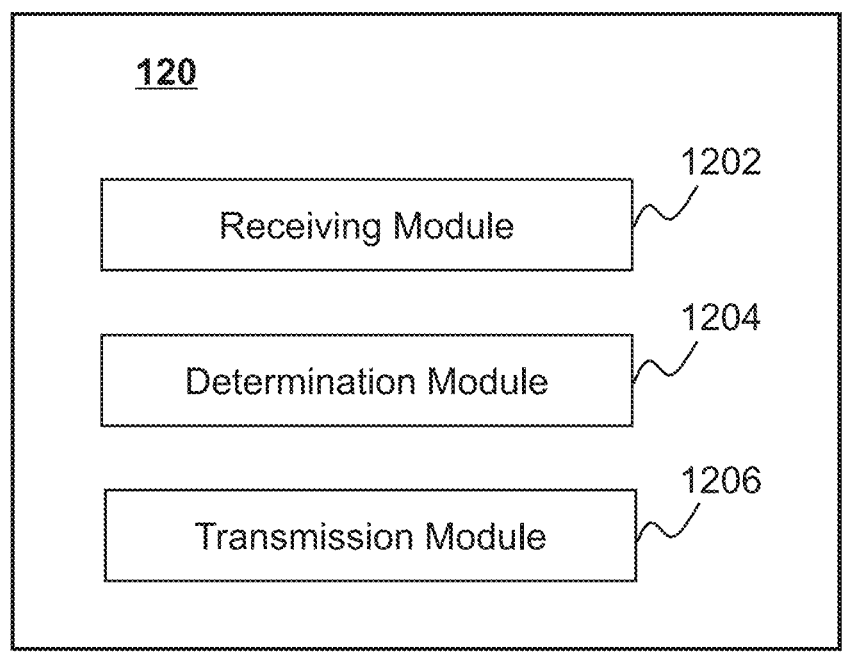
FIG. 12 is a block diagram illustrating an exemplary processing device according to some embodiments of the present disclosure.

FIG. 12 is a block diagram illustrating an exemplary processing device 120 according to some embodiments of the present disclosure. The processing device 120 may include a receiving module 1202, a determination module 1204, and a transmission module 1206. In some embodiments, at least a portion of the processing device 120 may be implemented on the computing device 300 as illustrated in FIG. 3 or the mobile device 400 as illustrated in FIG. 4.

The receiving module 1202 may be configured to receive information and/or signal related to the MRI system 100. For example, the receiving module 1202 may be configured to receive MR signals of a subject from one or more coil units. As another example, the receiving module 1202 may receive a motion signal relating to a physiological motion of the subject from a sensor before or during an MR scan of the subject. Merely by way of an example, the receiving module 1202 may receive an ECG signal from an ECG sensor and/or a respiratory signal from a respiratory signal detector. More descriptions regarding the receiving of the MR signals and/or the motion signal may be found elsewhere in the present disclosure. See, e.g., operations 1302 and 1310 and the relevant description thereof.

The determination module 1204 may be configured to determine a control signal based on the motion signal received from the sensor. The control signal may be used to control the MRI device. In some embodiments, the control signal may include one or more operation parameters, such as a time parameter, a radiation dose parameter, etc., relating to the operation of the MRI device. For example, the determination module 1204 may determine the control signal including an MR signal acquisition time based on the motion signal. The MR signal acquisition time may refer to a time point (or period) when the MRI device is controlled to execute an MR scan on the subject. More descriptions regarding the determination of the control signal may be found elsewhere in the present disclosure. See, e.g., operation 1304 and the relevant description thereof.

The transmission module 1206 may be configured to transmit information to one or more components of the MRI system. For example, the transmission module 1206 may transmit the control signal to the MRI device. In some embodiments, the transmission module 1206 may transmit the control signal to the MRI device directly or indirectly. For example, the transmission module 1206 may transmit the control signal to the MRI device directly to control the MRI device. As another example, the transmission module 1206 may transmit the control signal to a control device of the MRI device to control the MRI device.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may include one or more additional components (e.g., a storage module for data storing) and/or one or more components described above may be omitted. Additionally or alternatively, a module of the processing device 120 may be divided into two or more separate units or a plurality of modules of the processing device 120 may be integrated into a single module.

Figure 13:
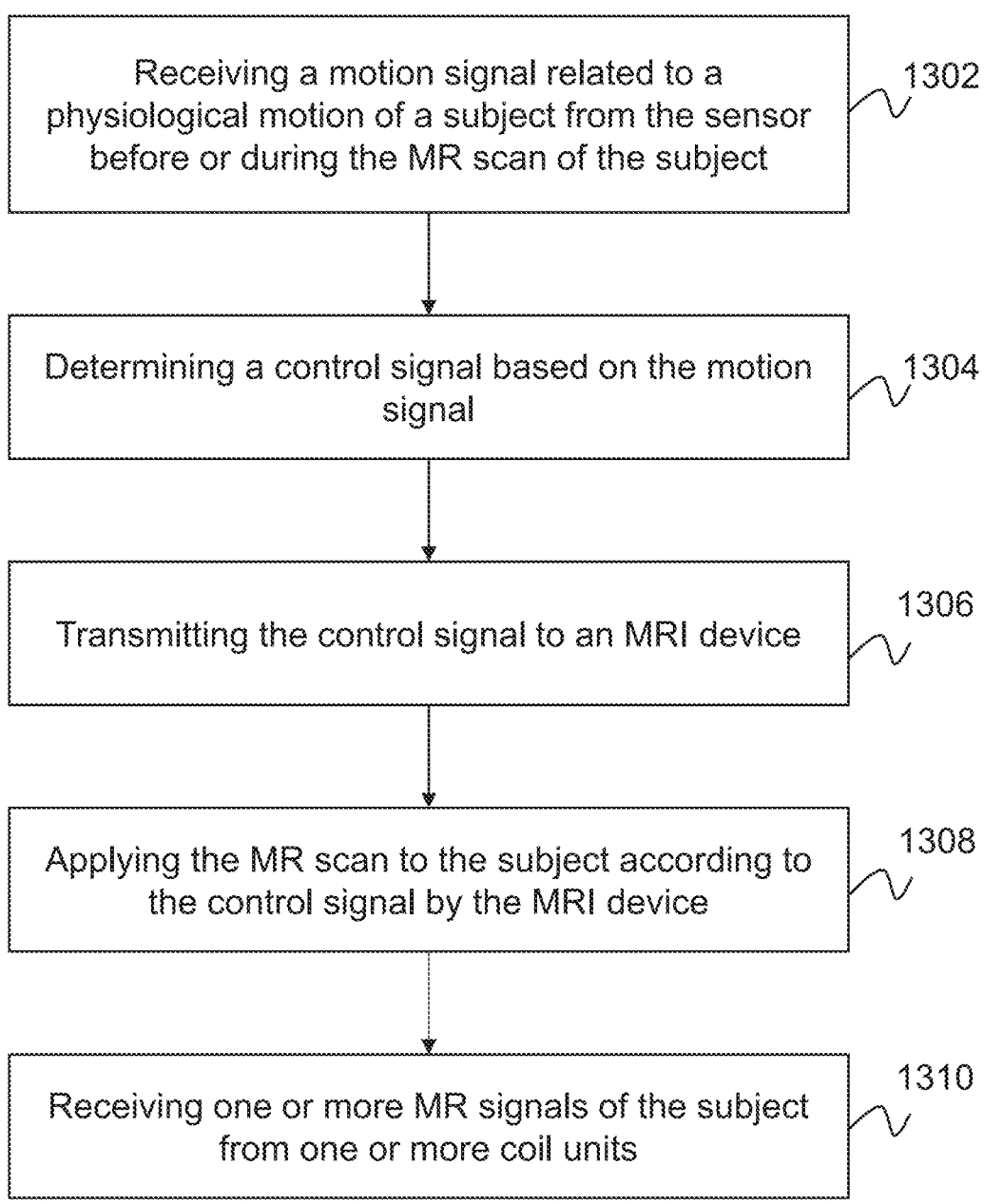
FIG. 13 is a flowchart illustrating an exemplary process for performing an MR scan on a subject according to some embodiments of the present disclosure.

FIG. 13 is a flowchart illustrating an exemplary process for performing an MR scan on a subject according to some embodiments of the present disclosure. In some embodiments, the process 1300 may be implemented in the MRI system 100 illustrated in FIG. 1. For example, the process 1300 may be stored in a storage device (e.g., the storage device 130 and/or the storage 320) of the MRI system 100 in the form of instructions, and invoked and/or executed by the processing device 120 (e.g., the processor 310 of the computing device 300 as illustrated in FIG. 3, the CPU 440 of the mobile device 400 as illustrated in FIG. 4, or one or more modules of the processing device 120 illustrated in FIG. 12).

The subject to be scanned may include any biological subject (e.g., a patient) or any non-biological subject (e.g., a man-made object). For example, the subject may include a specific portion of a patient, such as the head, the thorax, the abdomen of the patient, or the like, or a combination thereof. The MR scan may be performed on the subject by an MRI device (e.g., the MRI device 110) that includes a coil assembly (e.g., the coil assembly 112). The coil assembly may include a substrate (e.g., the substrate 510), one or more coil units (e.g., coil unit(s) 520), and a sensor (e.g., a sensor 530) mounted within or on the substrate. The substrate may be configured to position the coil assembly during the scan of the subject, for example, on the chest, the abdomen, and/or the back of the subject. The sensor may be configured to detect a motion signal during and/or before the MR scan.

In 1302, the processing device 120 (e.g., the receiving module 1202) may receive a motion signal relating to a physiological motion of the subject from the sensor before or during the MR scan of the subject.

The physiological motion of the subject may include a cardiac motion, a respiratory motion, a blood flow, a gastrointestinal motion, a skeletal muscle motion, a brain motion (e.g., a brain pulsation), or the like, or any combination thereof. The motion signal may be acquired by the sensor. For example, the motion signal may include an ECG signal detected by an ECG sensor that has the same or similar components of the ECG sensor 531 as discussed in FIGS. 5 and 6. As another example, the motion signal may include a respiratory signal detected by a respiratory signal detector that has the same or similar components of the respiratory signal detector 532 as discussed in FIG. 5.

In some embodiments, the processing device 120 may receive the motion signal from the sensor directly (e.g., via a signal transmission component of the sensor) or indirectly (e.g., via a network and/or another component of the MRI system 100). For example, a signal transmission component (e.g., the signal transmission component 550) of the sensor may transmit the motion signal to the processing device 120. As another example, the signal transmission component may transmit the motion signal to a control device (e.g., the control device 250), and the processing device 120 may receive the motion signal from the control device. In some embodiments, the processing device 120 may receive the motion signal from the sensor in real time or intermittently (e.g., periodically or irregularly).

In some embodiments, the motion signal received from the sensor may include the motion signal itself (e.g., an ECG signal represented by an ECG curve as indicated in FIG. 11), as well as information relating to the motion signal, such as a motion phase, a motion cycle, a motion amplitude, etc. Alternatively, the motion signal may include the motion signal itself and the processing device 120 may generate the information relating to the motion signal by processing the motion signal. For example, the processing device 120 may identify a cardiac cycle, systole and/or diastole in the cardiac cycle based on an ECG signal.

In 1304, the processing device 120 (e.g., the determination module 1204) may determine a control signal based on the motion signal received from the sensor.

The control signal may be used to control the MRI device. For example, the control signal may be used to cause the MR device to start an MR scan, terminate or pause an MR scan, or the like, or any combination thereof. In some embodiments, the control signal may control the one or more components of the MRI device, such as a magnetic body, a gradient coil, and an emitting coil, so as to control the MRI device. In some embodiments, the control signal may include one or more operation parameters, such as a time parameter, a radiation dose parameter, etc., relating to the operation of the MRI device.

As aforementioned, MR signals acquired in a time point (or period) when the physiological motion of the subject is smooth may be less affected by the physiological motion and result in fewer motion artifacts in an MR image generated based on the MR signals so acquired. Thus, it is desirable to determine the time point (or period) in which the physiological motion of the subject is smooth based on the motion signal. For example, the physiological motion at a certain time point may be regarded as being smooth if the motion amplitude at the certain time point is smaller than a first threshold. As another example, the physiological motion in a certain period may be regarded as being smooth if, for example, the period is within a smooth period of the physiological motion, a change of the motion amplitude of the physiological motion within the period is smaller than a second threshold, or the like. As yet another example, the physiological motion in consecutive motion cycles may be regarded as being smooth if, for example, an amplitude difference at the same motion phases in the consecutive motion cycles is below a third threshold, or the like.

In some embodiments, the processing device 120 may determine the MR signal acquisition time based on the motion signal. The MR signal acquisition time may refer to a time point (or period) when the MRI device is controlled to execute an MR scan on the subject. For example, the MR signal acquisition time may include a time point or period in which the physiological motion of the subject is smooth. The processing device 120 may further and transmit the control signal to the MRI device at the MR signal acquisition time, wherein the control signal may cause the MRI device to execute the MR scan immediately after the control signal is received. As another example, the processing device 120 may determine a control signal including the MR signal acquisition time, and transmit the control signal to the MRI device, wherein the control signal may cause the MRI device to execute the MR scan at the MR signal acquisition time. In some embodiments, the MR signal acquisition time may be a continuous period or a discontinuous time period. By determining a suitable MR signal acquisition time based on the motion signal, an image reconstructed based on MR signals detected in the MR scan may have less motion artifact and higher quality. This technique for reducing motion artifact may be referred to as a prospective correction technique or a triggering correction technique.

In some embodiments, the motion signal may include an ECG signal relating to the cardiac motion of the subject. A diastole or a portion of the diastole (e.g., a mid-later period in the diastole) may be regarded as a smooth period of cardiac motion as described in connection with FIG. 11. The MR signal acquisition time may be determined based on the smooth period and the ECG signal. For example, before the MR scan, the processing device 120 may predict the diastole in a next cardiac cycle as a first MR signal acquisition time based on the current cardiac cycle, and transmit a control signal to the MR device at the first MR signal acquisition time to actuate the MR scan. As another example, during the MR scan, the motion signal may be transmitted to the processing device 120 in real-time. The processing device 120 may identify a peak of an R-wave in the current cardiac cycle. The processing device 120 may further generate a control signal including a second MR signal acquisition time that begins after a certain period from the peak of the R-wave and lasts for a certain period. The control signal may be transmitted to the MRI device 110 immediately after it is generated and direct the MRI device 110 to execute the MR scan at the second MR signal acquisition time.

In some embodiments, the motion signal may include a respiratory signal relating to the respiratory motion of the subject. Normally, in a respiratory cycle, from an end-exhalation to an end-inhalation, the motion amplitude may increase from a lowest value to a highest value. A period in which the motion amplitude is below a threshold amplitude may be identified and regarded as a period in which the respiratory motion of the subject is smooth. Additionally or alternatively, the lungs normally remain stationary or substantially stationary in a smooth period of respiratory motion, which lasts from a time point in exhalation (e.g., a time point in a mid-later period in the exhalation) of the current respiratory cycle to the beginning of inhalation in a next respiratory cycle. In some embodiments, the respiratory signal may be received from the sensor before and/or during the MR scan, and the determination of the MR signal acquisition time based on respiratory signal may be performed in a similar manner as that based on an ECG signal described above.

In some embodiments, the processing device 120 may determine whether the physiological motion of the subject is not smooth according to the motion signal. For example, the processing device 120 may determine that the physiological motion is not smooth at a certain time point if, for example, the motion amplitude at the certain time point is greater than the first threshold. As another example, the physiological motion in a certain period may be regarded as being not smooth if, for example, the period is out of the smooth period of the physiological motion, a change of the motion amplitude of the physiological motion within the period is greater than the second threshold, or the like. As yet another example, the physiological motion in consecutive motion cycles may be regarded as being unsmooth if, for example, an amplitude difference at the same motion phases in the consecutive motion cycles is greater than the third threshold, or the like.

In response to a determination that the physiological motion of the subject is unsmooth, the processing device 120 may determine and transmit a control signal to cause the MR device to terminate or pause the MR scan. Optionally, the processing device 120 may also transmit a notification regarding the unsmooth physiological motion (e.g., a notification to reminder a user to help the subject to adjust breathing) to a user terminal (e.g., a terminal 140). The notification may notify a user regarding the occurrence of the unsmooth physiological motion, the termination or pause of the MR scan, provide a reminder to a patient to calm down or adjust breathing, or how to make the MR scan to re-start or resume (e.g., by adjusting breathing), or the like, or a combination thereof.

Additionally or alternatively, the processing device 120 may determine whether the physiological motion is abnormal according to the motion signal. For example, if the physiological motion at a certain time point is greater than a fourth threshold (which is greater than the first threshold) and/or an amplitude change during a period is greater than a fifth threshold (which is greater than the second threshold), the physiological motion may be regarded as being abnormal. In response to a determination that the physiological motion is abnormal, the processing device 120 may generate a control signal to terminate (or pause) the MR scan. In some embodiments, if the physiological motion is determined to be unsmooth but not abnormal during the MR scan, the processing device 120 may generate a control signal to continue the MR scan, and correct a reconstructed MR image based on the motion signal using a retrospective motion correction technique as described hereinafter.

In 1306, the processing device 120 (e.g., the transmission module 1206) may transmit the control signal to the MRI device.

In some embodiments, the control signal may be transmitted to the MRI device 110 directly or indirectly. For example, the processing device 120 may transmit the control signal to a control device (e.g., the control device 250), and the control device may control the MRI device. In some embodiments, the control signal may be associated with an MR signal acquisition time as described in connection with operation 1304, and the control signal may be transmitted to the MRI device at or before the MR signal acquisition time.

In 1308, the MR scan may be applied to the subject by the MRI device according to the control signal.

For example, in response to a control signal including an MR signal acquisition time, the MRI device may apply an MR pulse sequence on the subject at the MR signal acquisition time to obtain MR signals. As another example, during an MR scan, in response to a control signal to terminate (or pause) the MR scan, the MRI device may stop emitting RF pulses and terminate (or pause) the MR scan.

In 1310, the processing device 120 (e.g., the receiving module 1202) may receive MR signals of the subject from one or more coil units. For example, the processing device 120 may receive the MR signal(s) from the coil unit(s) directly or via one or more other components (e.g., the network 150 and/or a signal transmission component of the coil assembly).

In some embodiments, the processing device 120 may further reconstruct an MR image of the subject based on the MR signals and the motion signal. A compensation correction technique (or also referred to as a prospective correction technique) may be applied in the image reconstruction based on the motion signal to reduce motion artifact due to the physiological motion (e.g., heartbeat and/or breathing). For example, during the acquisition of the MR signals, a respiratory signal of the subject may be detected and assigned to the MR signals. Based on the respiratory signal, only MR signals that fulfill a certain condition, for example, being detected in a period in which the physiological motion is smooth (e.g., the motion amplitude being smaller than a threshold) may be identified from the MR signals. The MR image of the subject may be reconstructed based on the identified MR signals. As another example, MR signals corresponding to a same motion phase or similar motion phases (e.g., consecutive motion phases) may be identified based on the motion signal, and an MR image corresponding to the motion phase(s) may be generated based on the identified MR signals. Alternatively, the processing device 120 may determine a plurality of sets of MR signals from the detected MR signals, wherein each set corresponds to a motion phase of a motion cycle. The processing device 120 may further generate a plurality of MR images corresponding to the motion phases based on the sets of MR signals. Merely by way of example, based on an ECG signal, twenty sets of MR signals corresponding to twenty cardiac phases in a cardiac cycle may be determined. Each set of MR signal corresponding to a cardiac phase may be used to reconstruct an MR image of the corresponding cardiac phase. Optionally, the MR images corresponding to different cardiac phases may be displayed in sequence to dynamically show the cardiac motion of the subject.

In some embodiments, the motion signal may include a respiratory signal. The processing device 120 may utilize a respiratory compensation technique, such as a respiratory ordered phase encoding (ROPE) technique, a centrally ordered phase encoding (COPE) technique, a hybrid ordered phase encoding (HOPE), or the like, or any combination thereof in the MR image reconstruction. For example, based on a respiratory signal, the processing device 120 may apply a same phase encoding or similar phase encodings to MR signals corresponding to a same respiratory phase or similar respiratory phases in the MR image reconstruction. In this way, a random phase shift caused by the respiratory motion may be modified into a regular change. In the resulting MR image, motion artifacts may be eliminated or partially eliminated (e.g., with remaining artifacts located at the edge of the image).

It should be noted that the above descriptions regarding the process 1300 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1300 may be accomplished with one or more additional operations not described, and/or without one or more of the operations discussed may be omitted. In some embodiments, during an MR scan, the sensor may transmit the motion signal to the processing device 120 continuously or intermittently (e.g., periodically or irregularly). One or more of the operations 1302 to 1310 may be performed continuously or intermittently during the MR scan.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value."

What is claimed is:

1. A system for a magnetic resonance imaging (MRI), comprising:
    a substrate configured to position one or more coil units of an MRI device during an MR scan of a subject, the one or more coil units being mounted within or on the substrate; and
    a sensor mounted within or on the substrate, the sensor being configured to detect a motion signal relating to a physiological motion of the subject before or during the MR scan;
    a signal transmission component configured to receive the motion signal from the sensor and transmit the motion signal to a control device of the MRI device;
    the control device configured to control the MRI device to apply the MR scan on the subject according to the motion signal;
    the one or more coil units configured to receive MR signals from the subject during the MR scan and transmit the MR signals to a processing device; and
    the processing device configured to receive the MR signals from the one or more coil units, reconstruct an MR image of the subject based on the MR signals, and cause a display to present the MR image.

2. A method for magnetic resonance imaging (MRI) implemented on a computing device having at least one processor and at least one storage device, the method comprising:
    receiving, by the at least one processor, a motion signal relating to a physiological motion of a subject, wherein the motion signal is collected by a sensor before or during a magnetic resonance (MR) scan of the subject, the sensor is mounted on or within a substrate of a coil assembly of an MRI device, and the substrate positions the coil assembly on the subject before the MR scan;
    determining, by the at least one processor, based on the motion signal, an MR signal acquisition time;
    directing, by the at least one processor, the MRI device to execute the MR scan on the subject at the MR signal acquisition time to collect MR signals from the subject;
    reconstructing, by the at least one processor, an MR image of the subject based on the MR signals; and
    causing, by the at least one processor, a display to present the MR image.

3. A coil assembly of a magnetic resonance imaging (MRI) device, wherein the MRI device is configured to perform a magnetic resonance (MR) scan on a subject, and the coil assembly comprises:
    a substrate configured to position one or more coil units during the MR scan of the subject, the one or more coil units being mounted within or on the substrate; and
    a sensor mounted within or on the substrate, the sensor being configured to detect a motion signal relating to a physiological motion of the subject before or during the MR scan, wherein the substrate includes at least one of fabric, plastic, polyethylene (PE), polypropylene (PP), polyester, ethylene-vinyl acetate (EVA), polybutylene terephthalate (PBT), polycarbonate (PC), polyoxymethylene (POM), polyurethane (PU), polystyrene (PS), nylon, cotton, fiber, or resin;
    the one or more coil units configured to receive MR signals from the subject during the MR scan and transmit the MR signals to a processing device, the processing device being configured to receive the MR signals from the one or more coil units, reconstruct an MR image of the subject based on the MR signals, and cause a display to present the MR image.

4. The system of claim 1, wherein:
    the substrate includes a proximal surface and a distal surface with respect to the subject, the proximal surface and the distal surface being opposite to each other, and
    the sensor is mounted on the proximal surface of the substrate.

5. The system of claim 1, wherein the physiological motion includes a cardiac motion of the subject, the sensor includes an electrocardiogram (ECG) sensor configured to detect a signal relating to the cardiac motion of the subject.

6. The system of claim 1, wherein the physiological motion includes a respiratory motion of the subject, and the sensor includes a respiratory signal detector configured to detect a signal relating to the respiratory motion of the subject.

7. The system coil assembly of claim 1, further comprising an MR signal processing device, wherein:
    the MR signal processing device is operably connected to the one or more coil units and the signal transmission component,
    the MR signal processing device is configured to process the MR signal and transmit the processed MR signal to the signal transmission component, and
    the signal transmission component is further configured to transmit the processed MR signal to the control device.

8. The system of claim 1, wherein the substrate includes two or more layers that form a chamber, and at least a portion of the one or more coil units and the sensor is mounted within the chamber.

9. The system of claim 1, wherein the substrate includes a circuit board mounted within the substrate, and the sensor is mounted on the circuit board.

10. The system of claim 1, wherein the sensor configured to detect the motion signal is part of the one or more coil units.

11. The method of claim 2, wherein the determining, based on the motion signal, an MR signal acquisition time comprises:
    determining, based on the motion signal, a smooth period in which the physiological motion of the subject is smooth; and determining the smooth period as the MR signal acquisition time.

12. The method of claim 2, wherein the physiological motion includes a cardiac motion of the subject and/or a respiratory motion of the subject, the sensor includes an electrocardiogram (ECG) sensor configured to detect a signal relating to the cardiac motion of the subject and/or a respiratory signal detector configured to detect a signal relating to the respiratory motion of the subject.

13. The system of claim 5, wherein the ECG sensor further comprises:
   a signal emitter configured to emit a reference signal toward the subject, the reference signal being reflected by the subject; and
   a signal receiver configured to receive at least a portion of the reflected reference signal from the subject.

14. The system of claim 6, wherein the respiratory signal detector comprises:
   a motion sensor configured to detect a signal relating to the respiratory motion of the subject, the motion sensor including at least one of a pressure sensor, an accelerometer, a speed sensor, or a gravity sensor; and
   a pad configured to accommodate the motion sensor.

15. The system of claim 7, wherein the MR signal processing device comprises:
   a low noise amplifier (LNA) configured to amplify the MR signal; and
   a filter configured to generate the processed MR signal by filtering the amplified MR signal.

16. The method of claim 11, wherein
   the motion signal includes an ECG signal relating to a cardiac motion of the subject, and the smooth period includes at least a portion of the diastole of the subject, or
   the motion signal includes a respiratory signal relating to a respiratory motion of the subject, and the smooth period includes a period in which a respiratory amplitude is below a threshold amplitude.

17. The system of claim 13, wherein the signal emitter comprises:
   a signal generator configured to generate a preliminary reference signal;
   a signal amplifier configured to generate the reference signal by amplifying the preliminary reference signal; and
   a transmitting antenna configured to emit the reference signal toward the subject.

18. The system of claim 13, wherein the signal receiver comprises:
   a receiving antenna configured to receive the at least a portion of the reflected reference signal;
   a signal amplifier configured to amplify the received portion of the reflected reference signal; and
   a signal mixer configured to generate a mixed signal by mixing the reference signal with the amplified portion of the reflected reference signal, the mixed signal being the signal relating to the cardiac motion of the subject.

19. The system of claim 13, wherein:
   the signal receiver further comprises:
      a receiving antenna configured to receive at least a portion of the reflected reference signal;
      a signal amplifier configured to amplify the received portion of the reflected reference signal; and
      a signal mixer configured to generate a mixed signal by mixing the reference signal with the amplified portion of the reflected reference signal, and
   the MRI device further comprises a signal processing component configured to determine the signal relating to the cardiac motion of the subject based on the mixed signal.

20. The system of claim 13, wherein at least a portion of the signal receiver is integrated into the one or more coil units.

* * * * *